(12) United States Patent
Lim

(10) Patent No.: US 12,364,777 B2
(45) Date of Patent: Jul. 22, 2025

(54) HOMODIMERIC ANTIBODIES FOR USE IN TREATING CANCERS AND METHODS OF USE

(71) Applicant: Medicovestor, Inc., Wilmington, DE (US)

(72) Inventor: Seah Lim, Wilmington, DE (US)

(73) Assignee: MEDICOVESTOR, INC., Wilmington, DE (US)

( * ) Notice: Subject to any disclaimer, the term of this patent is extended or adjusted under 35 U.S.C. 154(b) by 0 days.

(21) Appl. No.: 18/426,199

(22) Filed: Jan. 29, 2024

(65) Prior Publication Data

US 2025/0127942 A1   Apr. 24, 2025

Related U.S. Application Data

(60) Provisional application No. 63/614,765, filed on Dec. 26, 2023, provisional application No. 63/592,048, filed on Oct. 20, 2023.

(51) Int. Cl.
| | | |
|---|---|---|
| A61K 47/68 | (2017.01) |
| A61K 39/00 | (2006.01) |
| A61K 51/00 | (2006.01) |
| A61K 51/10 | (2006.01) |
| A61P 35/00 | (2006.01) |

(52) U.S. Cl.
CPC ...... *A61K 51/1072* (2013.01); *A61K 39/0011* (2013.01); *A61K 47/68033* (2023.08); *A61K 47/6863* (2017.08); *A61K 47/6889* (2017.08); *A61K 51/00* (2013.01); *A61P 35/00* (2018.01); *A61K 2121/00* (2013.01)

(58) Field of Classification Search
None
See application file for complete search history.

(56) References Cited

U.S. PATENT DOCUMENTS

| | | |
|---|---|---|
| 5,731,168 A | 3/1998 | Carter et al. |
| 5,877,296 A | 3/1999 | Hamann et al. |
| 6,565,827 B1 | 5/2003 | Kaminski et al. |
| 6,897,044 B1 | 5/2005 | Braslawsky |
| 7,405,077 B2 | 7/2008 | Lim |
| 7,422,739 B2 | 9/2008 | Anderson et al. |
| 7,446,190 B2 | 11/2008 | Sadelain et al. |
| 7,741,465 B1 | 6/2010 | Eshhar et al. |
| 8,088,387 B2 | 1/2012 | Steeves et al. |
| 8,277,806 B2 | 10/2012 | Lindhofer |
| 8,592,562 B2 | 11/2013 | Kannan et al. |
| 9,062,349 B2 | 6/2015 | Chiriva-Internati |
| 9,499,629 B2 | 11/2016 | June et al. |
| 9,505,848 B2 | 11/2016 | Davis et al. |
| 9,592,562 B2 | 3/2017 | Harif et al. |
| 9,862,769 B2 | 1/2018 | De Goeij et al. |
| 9,970,937 B2 | 5/2018 | Chiriva-Internati |
| 10,011,858 B2 | 7/2018 | Igawa et al. |
| 10,322,192 B2 | 6/2019 | Albone et al. |
| 10,344,050 B2 | 7/2019 | Gramer et al. |
| 10,517,960 B2 | 12/2019 | Jakobsen et al. |
| 10,596,270 B2 | 3/2020 | Stafford et al. |
| 10,597,464 B2 | 3/2020 | Labrijn et al. |
| 10,729,782 B2 | 8/2020 | Naito et al. |
| 10,752,683 B2 | 8/2020 | Ab et al. |
| 10,836,830 B2 | 11/2020 | Wilson et al. |
| 11,401,348 B2 | 8/2022 | Lazar et al. |
| 11,597,766 B2 | 3/2023 | Zugmaier et al. |
| 12,116,410 B1 | 10/2024 | Lim |
| 12,121,587 B1 | 10/2024 | Lim |
| 2002/0168662 A1 | 11/2002 | Lim et al. |
| 2005/0158828 A1 | 7/2005 | Braslawsky et al. |
| 2006/0115817 A1 | 6/2006 | Lim |
| 2007/0297978 A1 | 12/2007 | Chinn |
| 2010/0278834 A1 | 11/2010 | Lanzavecchia |
| 2012/0322135 A1 | 12/2012 | Uda et al. |
| 2013/0295113 A1 | 11/2013 | Mytych et al. |
| 2015/0038682 A1 | 2/2015 | Tsurushita |
| 2015/0274812 A1 | 10/2015 | Swem et al. |
| 2016/0032014 A1 | 2/2016 | Michaels et al. |
| 2017/0204194 A1 | 7/2017 | Chen et al. |
| 2017/0319690 A1 | 11/2017 | Wang et al. |
| 2018/0346555 A1 | 12/2018 | Orengo et al. |
| 2019/0322750 A1 | 10/2019 | Park et al. |
| 2020/0283524 A1 | 9/2020 | Xu et al. |

(Continued)

FOREIGN PATENT DOCUMENTS

| | | |
|---|---|---|
| WO | 2009/086320 A1 | 7/2009 |
| WO | 2014/144080 A2 | 9/2014 |

(Continued)

OTHER PUBLICATIONS

Caron et al., Engineered humanized dimeric forms of IgG are more effective antibodies. J Exp Med 176 (4): 1191-1195, 1992.*
Shopes, B., "A genetically engineered human IgG mutant with enhanced cytolytic activity.", J. of immunology, vol. 148, Issue. 9, 1992, pp. 2918-2922.
Shopes, B., "A genetically engineered human IgG with limited flexibility fully initiates cytolysis via complement.," Molecular Immunology, Apr. 1993, vol. 30, Issue. 6, pp. 603-609.
Van der Neut, K. M., "Anti-inflammatory activity of human IgG4 antibodies by dynamic Fab arm exchange.", Science, vol. 317, issue. 5844, Sep. 14, 2007, pp. 1554-1557.
Wolff, EA. et al., "Monoclonal antibody homodimers:enhanced antitumor activity in nude mice," Cancer Res., 1993, vol. 53, Issue. 11, pp. 2560-2565.

(Continued)

*Primary Examiner* — Ruixiang Li
(74) *Attorney, Agent, or Firm* — HOLLAND & HART LLP

(57) ABSTRACT

This disclosure relates to homodimeric antibodies for use in treating cancer generally and to both homodimeric antibodies that bind human sperm protein 17 (Sp17) and homodimeric antibody immunoconjugates specifically. Such homodimeric antibodies display improved properties relative to monomeric antibodies, for example, because they can crosslink cells, improve cellular uptake, and/or carry greater payloads.

21 Claims, 10 Drawing Sheets

Specification includes a Sequence Listing.

(56) References Cited

U.S. PATENT DOCUMENTS

| | | |
|---|---|---|
| 2021/0040235 A1 | 2/2021 | Kadouche et al. |
| 2023/0201210 A1 | 6/2023 | Sliwkowski et al. |
| 2023/0391882 A1 | 12/2023 | Urech et al. |
| 2025/0011403 A1 | 1/2025 | Lim |
| 2025/0011460 A1 | 1/2025 | Lim |

FOREIGN PATENT DOCUMENTS

| | | | |
|---|---|---|---|
| WO | 2016/111645 A1 | 7/2016 | |
| WO | 2017/013231 A1 | 1/2017 | |
| WO | 2017/015634 A2 | 1/2017 | |
| WO | 2019/016392 A1 | 1/2019 | |
| WO | 2022/076669 A1 | 4/2022 | |
| WO | 2022/096716 A2 | 5/2022 | |
| WO | 2022/116808 A1 | 6/2022 | |
| WO | 2022/235622 A2 | 11/2022 | |
| WO | 2023/166418 A2 | 9/2023 | |

OTHER PUBLICATIONS

Akbar et al., A compact vocabulary of paratope-epitope interactions enables predictability of antibody-antigen binding, Cell Reports Mar. 16, 2021, 34, 108856.

Almagro & Fransson, Humanization of Antibodies, Frontiers in Bioscience, 2008, 13:1619-33.

Altshuler et al., Generation of Recombinant Antibodies and Means for Increasing Their Affinity, Dept. Of. Biochemistry (Moscow), 2010, 75(13):1584-1605.

Casset et al., A peptide mimetic of an anti-CD4 monoclonal antibody by rational design, Biochemical and Biophysical Research Communications, 2003, 307:198-205.

Chiriva-Internati et al., Sperm protein 17 (SP17) in multiple myeloma: opportunity for myeloma-specific donor T cell infusion to enhance graft-versus-myeloma effect without increasing graft-versus-host disease risk, Eur. J. Immunol, Aug. 2001, 31(8):2277-83.

Chiriva-Internati et al., Tumor Vaccine for Ovarian Carcinoma Targeting Sperm Protein 17, Cancer, May 2002, 1;94(9):2447-53.

De Pascalis et al., Grafting of abbreviated complementarity determining regions containing specificity determining residues essential for ligand contact to engineer a less immunogenic humanzied monoclonal antibody, Journal of Immunology, 2002, vol. 169, pp. 3076-3084.

Edwards et al., The Remarkable Flexibility of the Human Antibody Repertoire; Isolation of Over One Thousand Different Antibodies to a Single Protein, BLyS, J Mol Biol, 2003, 334: 103-118.

Goel et al., Plasticity within the Antigen-Combining Site May Manifest as Molecular Mimicry in the Humoral Immune Response. Journal of Immunology, 2004, 173(12)7358-7367.

Gura, Systems for Identifying New Drugs Are Often Faulty, Science, 1997, 278:1041-1042.

Hasegawa et al., Single Amino Acid substitution in LC-CDR1 induces Russell body phneotype that attenuates cellular protein synthesis through elF2a phosphorylation and thereby downregulates IgG secretion despite operational secretory pathway traffic, MABS, 2017, vol. 9, No. 5, pp. 854-873.

Holm et al., Functional mapping and single chain construction of the anti-cytokeratin 8 monoclonal antibody TS1, Molecular Immunology, 2007, 1075-1084.

Kahn et al., Adjustable Locks and Flexible Keys: Plasticity of Epitope-Paratope Interactions in Germline Antibodies., Journal of Immunology, 2014, 192:5398-5405.

Lim et al., Sperm protein 17 is a novel cancer-testis antigen in multiple myeloma, Blood, Mar. 1, 2001, 97(5):1508-10.

Lippow et al., Computational design of antibody-affinity improvement beyond in vivo maturation, Nature Biotechnology, 2017, 25(10):1171-1176.

Lo et al., Conformational epitope matching and prediction based on protein surface spiral features, BMC Genomics, 2021, vol. 22, Article No. 116.

Maccallum et al., Antibody-antigen interactions: contact analysis and binding site topography, Journal of Molecular Biology, 1996, vol. 262, pp. 732-745.

Marchalonis et al., The antibody repertoire in evolution: Chance, selection, and continuity, Dev & Comp Immunol., 2006, 30:223-247.

Mariuzza. R.A et al., The Structural Basis of Antigen-Antibody Recognition, Ann. Rev. Biophys. Biphys. Chem., 1987, 16:139-159.

Marks et al., How repertoire data are changing antibody science, J. Biol. Chem. 2020, 295(29) 9823-9837.

Poosarla et al., Computational De Novo Design of Antibodies Binding to a Peptide With High Affinity., Biotech. Bioeng. 2017, 114(6}: 1331-1342.

Rader et al., A phage display approach for rapid antibody humanization: Designed combinatorial V gene libraries, PNAS. 1998, 95:8910-8915.

Rudikoff et al., Single Amino Acid Substitution Altering Antigen-Binding Specificity, PNAS, 1982, 79:1979-1983.

Straughn et al., Expression of Sperm Protein 17 (SP17) in Ovarian Cancer, Int. J. Cancer, Mar. 1, 2004, 108(6):805-11.

Sulea et al., Application of Assisted Design of Antibody and Protein Therapeutics (ADAPT) improves efficacy of a Clostridium difficile toxin A single-domain antibody, Scientific Reports, 2018, 8(260): 1-11.

Vajda et al., Progress toward improved understanding of antibody maturation, Current Opinion in Structural Biology, 2021, 67 pp. 226-231.

Zhang et al., Combined real time PCR and immunohistochemical evaluation of sperm protein 17 as a cancer-testis antigen, Eur. J. Haematol, Oct. 2004, 73(4):280-4 (Abstract).

U.S. Appl. No. 18/807,087, filed Aug. 16, 2024, Medicovestor, Inc.
U.S. Appl. No. 18/807,097, filed Aug. 16, 2024, Medicovestor, Inc.
U.S. Appl. No. 18/821,716, filed Aug. 30, 2024, Medicovestor, Inc.
U.S. Appl. No. 18/821,708, filed Aug. 30, 2024, Medicovestor, Inc.
U.S. Appl. No. 19/002,112, filed Dec. 26, 2024, Medicovestor, Inc.

"International Search Report and Written Opinion of the International Searching Authority," issued in connection with Intn'l Appl. No. PCT/US2024/036822, dated Dec. 17, 2024 (16 pages).

"International Search Report and Written Opinion of the International Searching Authority," issued in connection with Int'l Appl. No. PCT/US2024/036820, dated Oct. 2, 2024 (13 pages).

"International Search Report and Written Opinion of the International Searching Authority," issued in connection with Int'l Appl. No. PCT/US2024/036824, dated Dec. 17, 2024 (20 pages).

"International Search Report and Written Opinion of the International Searching Authority," issued in connection with Int'l Appl. No. PCT/US2024/045704, dated Dec. 11, 2024 (16 pages).

"International Search Report and Written Opinion of the International Searching Authority," issued in connection with Int'l Appl. No. PCT/US2024/052137, dated Feb. 5, 2025 (19 pages).

"International Search Report and Written Opinion of the International Searching Authority," issued in connection with Int'l Appl. No. PCT/US24/61935, dated Mar. 4, 2025 (21 pages).

"Invitation to pay additional fee of the International Searching Authority," issued in connection with Int'l Appl. No. PCT/US2024/036822, dated Sep. 23, 2024, (3 pages).

Rossi, et al., "Novel Designs of Multivalent Anti-CD20 Humanized Antibodies as Improved Lymphoma Therapeutics", Cancer res., Oct. 15, 2008, vol. 68, No. 20, pp. 8384-8392.

US Patent Office "Office Action", issued in connection with U.S. Appl. No. 18/408,414. dated Jan. 22, 2025 (19 pages).

US Patent Office "Office Action", issued in connection with U.S. Appl. No. 18/821,716. dated Jan. 17, 2025 (9 pages).

Yadav, et al., "Fabrication of alkoxysilane substituted polymer-modified disposable biosensing 2 platform: toward sperm protein 17 sensing as a new cancer biomarker", Talanta, Jun. 1, 2022, vol. 243, pp. 507-514.

Altschul, et al., "Gapped BLAST and PSI-BLAST: a new generation of protein database search programs", Nucleic Acids Res., vol. 25, 1997, pp. 3389-3402.

Altschul, et al., "Protein database searches using compositionally adjusted substitution matrices", Febs J., vol. 272, 2005, pp. 5101-5109.

(56) References Cited

OTHER PUBLICATIONS

Golay, J., et al., "Role of Fc Core Fucosylation in the Effector Function of IgG1 Antibodies", Frontiers in Immunology, vol. 13, Jun. 2022, 929895.

* cited by examiner

SEQUENCE LISTING

```
Sequence total quantity: 12
SEQ ID NO: 1            moltype = DNA  length = 369
FEATURE                 Location/Qualifiers
source                  1..369
                        mol_type = other DNA
                        organism = Synthetic construct
SEQUENCE: 1
caggtacagc tgcagcagtc aggggctgag gtgaagaagc ctgggtcctc ggtgaaggtc   60
tcctgcaagg cttctggagg caccttcagc agctatgcta tcagctgggt gcgacaggcc  120
cctgacaagg ggcttgagtg gatgggaagg atcatcccta tccttggtat agcaaactac  180
gcacagaagt tccagggcag agtcacgatt accgcggaca aatccacgag cacagcctac  240
atggagctga gcagcctgag atctgaggac acggccgtgt attactgtgc agacccctcc  300
gaagaggtgg tagctgctta cggtgctttt gatatctggg gccaagggac cacggtcacc  360
gtctcaagc                                                          369

SEQ ID NO: 2            moltype = DNA  length = 336
FEATURE                 Location/Qualifiers
source                  1..336
                        mol_type = other DNA
                        organism = Synthetic construct
SEQUENCE: 2
gaaattgtgc tgactcagtc tccactctcc ctgcccgtca gacctgggga gccggcctcc   60
atctcctgca gggctagtca gagcctcctg cgtagtgacg gattcaacta cttggattgg  120
tacctgcaga agccagggca gtctccacag ctcctgatct atttgggttc taatcgggcc  180
tccggggtcc ctgacaggtt cagtggcagt ggatcaggca cagattttac actgaaaatc  240
agcagagtgg aggctgagga tgttggggtt tattactgca tgcaagctgt acaaactccg  300
tacatttttg gccaggggac caagctggag atcaaa                            336

SEQ ID NO: 3            moltype = AA  length = 123
FEATURE                 Location/Qualifiers
source                  1..123
                        mol_type = protein
                        organism = Synthetic construct
SEQUENCE: 3
QVQLQQSGAE VKKPGSSVKV SCKASGGTFS SYAISWVRQA PGQGLEWMGR IIPILGIANY   60
AQKFQGRVTI TADKSTSTAY MELSSLRSED TAVYYCARPS EEVVAAYGAF DIWGQGTTVT  120
VSS                                                                123

SEQ ID NO: 4            moltype = AA  length = 112
FEATURE                 Location/Qualifiers
source                  1..112
                        mol_type = protein
                        organism = Synthetic construct
SEQUENCE: 4
EIVLTQSPLS LPVRPGEPAS ISCRASQSLL RSDGFNYLDW YLQKPGQSPQ LLVYLGSNRA   60
SGVPDRFSGS GSGTDFTLKI SRVEAEDVGV YYCMQAVQTP YIFGQGTKLE IK          112

SEQ ID NO: 5            moltype = AA  length = 10
FEATURE                 Location/Qualifiers
source                  1..10
                        mol_type = protein
                        organism = Synthetic construct
SEQUENCE: 5
GGTFSSYAIS                                                          10

SEQ ID NO: 6            moltype = AA  length = 17
FEATURE                 Location/Qualifiers
source                  1..17
                        mol_type = protein
                        organism = Synthetic construct
```

```
SEQUENCE: 6
RIIPILGIAN YAQKFQG                                                             17

SEQ ID NO: 7            moltype = AA  length = 16
FEATURE                 Location/Qualifiers
source                  1..16
                        mol_type = protein
                        organism = Synthetic construct
SEQUENCE: 7
ARPSEEVVAA YGAFDI                                                              16

SEQ ID NO: 8            moltype = AA  length = 16
FEATURE                 Location/Qualifiers
source                  1..16
                        mol_type = protein
                        organism = Synthetic construct
SEQUENCE: 8
RASQSLLRSD GFNYLD                                                              16

SEQ ID NO: 9            moltype = AA  length = 7
FEATURE                 Location/Qualifiers
source                  1..7
                        mol_type = protein
                        organism = Synthetic construct
SEQUENCE: 9
LGSNRAS                                                                         7

SEQ ID NO: 10           moltype = AA  length = 10
FEATURE                 Location/Qualifiers
source                  1..10
                        mol_type = protein
                        organism = Synthetic construct
SEQUENCE: 10
MQAVQTPYIF                                                                     10

SEQ ID NO: 11           moltype = AA  length = 472
FEATURE                 Location/Qualifiers
source                  1..472
                        mol_type = protein
                        organism = synthetic construct
SEQUENCE: 11
MDMRVPAQLL GLLLLWLRGA RCQVQLQQSG AEVKKPGSSV KVSCKASGGT FSSYAISWVR              60
QAPGQGLEWM GRIIPILGIA NYAQKFQGRV TITADKSTST AYMELSSLRS EDTAVYYCAR             120
PSEEVVAAYG AFDIWGQGTT VTVSSASTKG PSVFPLAPCS RSTSESTAAL GCLVKDYFPE             180
PVTVSWNSGA LTSGVHTFPA VLQSSGLYSL SSVVTVPSSS LGTKTYTCNV DHKPSNTKVD             240
KRVESKYGPP CPPCPAPEFL GGPSVFLFPP KPKDTLMISR TPEVTCVVVD VSQEDPEVQF             300
NWYVDGVEVH NAKTKPREEQ FNSTYRVVSV LTVLHQDWLN GKEYKCKVSN KGLPSSIEKT             360
ISKAKGQPRE PQVYTLPPSQ EEMTKNQVSL TCLVKGFYPS DIAVEWESNG QPENNYKTTP             420
PVLDSDGSFF LYSRLTVDKS RWQEGNVFSC SVMHEALHNH YTQKSLSLSL GK                    472

SEQ ID NO: 12           moltype = AA  length = 241
FEATURE                 Location/Qualifiers
source                  1..241
                        mol_type = protein
                        organism = synthetic construct
SEQUENCE: 12
MDMRVPAQLL GLLLLWLRGA RCEIVLTQSP LSLPVRPGEP ASISCRASQS LLRSDGFNYL              60
DWYLQKPGQS PQLLVYLGSN RASGVPDRFS GSGSGTDFTL KISRVEAEDV GVYYCMQAVQ             120
TPYIFGQGTK LEIKRTVAAP SVFIFPPSDE QLKSGTASVV CLLNNFYPRE AKVQWKVDNA             180
LQSGNSQESV TEQDSKDSTY SLSSTLTLSK ADYEKHKVYA CEVTHQGLSS PVTKSFNRGE             240
C                                                                            241
```

HOMODIMERIC ANTIBODIES FOR USE IN TREATING CANCERS AND METHODS OF USE

CROSS-REFERENCE TO RELATED APPLICATIONS

This application claims the benefit of U.S. Provisional Patent Application No. 63/592,048, filed Oct. 20, 2023, and U.S. Provisional Patent Application No. 63/614,765, filed Dec. 26, 2023, each of which is incorporated, in its entirety, by this reference.

SEQUENCE LISTING

This disclosure includes a sequence listing, which has file name "Sequence_Listing_1200590014.xml," which was created on Jan. 29, 2024, which has a file size of 13,151 bytes, and which is incorporated by reference in its entirety.

FIELD OF THE INVENTION

The present disclosure relates to homodimeric antibodies for use in treating cancer and immunoconjugates thereof.

BACKGROUND OF SOME ASPECTS OF THE SPECIFICATION

Therapeutic antibodies are responsible for tremendous improvements in cancer outcomes and present new opportunities to cure cancer, at least in a subset of patients. The first antibody cancer immunotherapeutic Rituxan® was approved to treat B-cell non-Hodgkin's lymphoma in the United States in 1997 and has over $100 billion in lifetime sales. Rituxan® still sells over $1 billion annually despite extensive competition. The competing antibody Zevalin®, for example, was approved in the United States in 2002. Both Rituxan® and Zevalin® target CD20, which is a B-cell antigen, and both immunotherapeutics act by depleting B-cells. When Rituxan® binds CD20, it triggers antibody-dependent cellular toxicity and leukocyte-mediated cell death, whereas Zevalin® is chemically modified to chelate a radioisotope, which additionally allows for radiation-induced cell death. Therapeutic antibodies may also be conjugated to cytotoxic pharmaceuticals, for example, with labile linkers that allow antibody-drug conjugates that release their cytotoxic payloads upon binding to an antigen. Bispecific therapeutic antibodies bind two antigens such as both a cancer antigen and a T-cell receptor to allow for T-cell mediated cytotoxicity. Numerous other antibody-based strategies exist as cancer treatments.

While therapeutic antibodies revolutionized the field of oncology, progress remains incremental. Cancer is not yet cured. Innovative strategies that improve upon existing antibody technologies remain desirable.

SUMMARY OF SOME ASPECTS OF THE SPECIFICATION

Various aspects of this disclosure relate to the discovery of advantages provided by homodimeric antibodies that improve one or both of their administration and their efficacy relative to conventional therapeutic antibodies. Most therapeutic antibodies are based on immunoglobulin G (IgG) antibodies, which each have two antigen-binding sites. A conventional therapeutic antibody can therefore bind two antigens. The term "homodimeric antibody" as used in this specification refers to a covalently-crosslinked dimer of two antibodies such as two IgG antibodies. A homodimeric IgG antibody can therefore bind four antigens. The antigen is typically the same for each antigen-binding site of a homodimeric antibody, and thus, a homodimeric IgG antibody can typically bind four copies of the same antigen. This disclosure nevertheless contemplates homodimeric antibodies that comprise two bispecific IgG antibodies, which homodimeric antibodies would bind two copies of two different antigens.

Homodimeric antibodies display varying pharmacokinetic properties and avidity relative to their monomeric constituents. Homodimeric antibodies also have about twice the molecular weight of their monomeric constituents. These factors combine to both favorably alter the administration and efficacy of homodimeric antibodies in unpredictable ways that were not previously appreciated.

Without limiting this disclosure or any patent claim that matures from this disclosure, the inventors have found that homodimeric antibodies that bind cancer antigens are more favorable than conventional antibodies because homodimeric antibodies can cross-link cancer cells, which can inhibit metastasis that spreads cancer to other parts of the body and also inhibit the escape of the cancer from a localized intervention or immune response. A homodimeric antibody may be administered immediately prior to or during an ablative or other surgical intervention, for example, to cross-link cancer cells and inhibit individual cancer cells from escaping removal or destruction and forming metastases.

Previously-unappreciated confounding variables of using naked homodimeric antibodies as cancer immunotherapeutics include the relative orientation and steric crowding of the Fc portions of their constituent antibodies. When a conventional immunotherapeutic antibody binds a cell-surface antigen on a cancer cell, the Fc portion of the antibody generally points away from the cancer cell, which presents the Fc portion to leukocytes that mediate cell death. When a homodimeric antibody crosslinks cancer cells, however, the Fc portions of the homodimeric antibody may become sequestered between the cancer cells, which impedes leukocytes from binding to the Fc portions and mediating cell death. Different cross-linking strategies may also mask the Fc portions of a homodimeric antibody, for example, by sterically blocking interactions between an Fc region and Fc receptors. A certain portion of randomly-crosslinked homodimeric antibodies will be incapable of binding Fc receptors, and such homodimeric antibodies would therefore be incapable of causing Fc-receptor-mediated cell death. Even with flexible, thoughtfully-positioned linkers designed to maintain Fc-receptor accessibility, the steric bulk and relative orientation of a cell-surface antigen may nevertheless result in conformations that limit the accessibility of the Fc portions of a homodimeric antibody to Fc receptors. Indeed, over thirty years have passed since homodimeric antibodies were first proposed as cancer immunotherapeutics (see, for example, Wolff, E A et al., "Monoclonal antibody homodimers: enhanced antitumor activity in nude mice," CANCER RES. 1993; 53(11):2560-65), and yet no homodimeric antibody has ever displayed efficacy against cancer in humans. However, the possible limit in accessibility of the Fc portions of a homodimeric could be leveraged to reduce any non-specific Fc binding if the antibody is conjugated to a payload as in antibody-drug conjugate, especially in the reticulo-endothelial system such as liver, hence reducing the nonspecific side-effects of the antibody-drug conjugate.

In view of the confounding problems set forth in the preceding paragraph, this disclosure features homodimeric antibody immunoconjugates that do not require Fc-receptor-mediated pathways. Conventional immunoconjugates advantageously allow both Fc-receptor-mediated cell death and cytotoxicity as a result of their radioactive or pharmaceutical payloads. The conjugate of a conventional immunoconjugate is generally orders of magnitude smaller than a second antibody of a homodimeric antibody, and thus, conventional immunoconjugates generally allow ample steric accessibility to Fc receptors. Homodimeric antibody immunoconjugates display reduced Fc-receptor accessibility, and thus, it was previously unknown whether a homodimeric antibody immunoconjugate might display efficacy that is comparable to either a conventional naked antibody or a conventional immunoconjugate.

Small changes to an Fc portion of an antibody display profound effects. Relatively conservative point mutations to an antibody Fc region significantly affect pharmacokinetics (see, for example, International Application Publication No. WO 2009/086320 A1). Relatively small changes in the glycosylation of an Fc region display significant effects on Fc-receptor mediated cell death (see, for example, Golay, J. et al., "Role of Fc Core Fucosylation in the Effector Function of IgG1 Antibodies" FRONT. IMMUNOL. 2022; 13:929895). Larger changes might be expected to critically impair one or both of pharmacokinetics and Fc-receptor-mediated cell death. Whether homodimeric immunoconjugates might nevertheless allow for appreciable clinical efficacy in spite of significantly larger structural changes was previously unknown.

Without limiting this disclosure or any patent claim that matures from this disclosure, the inventors have found that homodimeric antibody immunoconjugates that bind cancer antigens are more favorable than conventional naked antibodies and immunoconjugates, for example, because additional binding sites favor clustering of cell-surface antigens and resultant endocytosis, which sequesters the immunoconjugate inside a cancer cell to favor cell death. Sequestering an immunoconjugate that comprises a radioisotope within a cancer cell both accelerates death of the cancer cell and protects other cells from the radiation. Many immunoconjugates that comprise pharmaceutical agents include labile linkers that are engineered to release the pharmaceutical agents upon endocytosis, for example, in response to the pH of an endocytic vesicle or in response to a hydrolase or other enzyme of a vesicle. Homodimeric antibody immunoconjugates can accelerate release of pharmaceutical agents that become labile upon endocytosis by favoring clustering that results in endocytosis.

Without limiting this disclosure or any patent claim that matures from this disclosure, the inventors unexpectedly found that homodimeric antibody immunoconjugates display robust activity at killing cancer cells even in the absence of Fc-receptor-mediated cytotoxicity. In many applications, homodimeric antibody immunoconjugates display improved clinical efficacy relative to both conventional naked antibodies and conventional immunoconjugates, which was unexpected, for example, due to the compromised Fc-receptor-mediated cytotoxicity of a homodimeric antibody.

Another unexpected advantage of homodimeric antibodies generally and homodimeric antibody immunoconjugates specifically is that one, two, or each of their improved efficacy, pharmacokinetics, and pharmacodynamics allow for reduced infusion times relative to conventional antibodies and antibody immunoconjugates. Therapeutic antibodies used as cancer immunotherapeutics are frequently infused intravenously over a period of time such as several hours. As the development of therapeutic antibodies and other infused therapeutic interventions increases, the capacity of infusion centers has become limiting. Pharmacological interventions that can be administered over shorter periods of time relative to comparable interventions can therefore reduce the burden on infusion centers, reduce costs, and improve patient experiences independent from the improved clinical outcomes described herein.

Without limiting this disclosure or any patent claim that matures from this disclosure, homodimeric antibodies may also increase the cytotoxicity of cancer cells by increasing the number of antibodies that bind to the cancer cells since it is possible that not all of the binding domains of the antibody making up the homodimers will be used when binding an antigen. This may overcome some of the obstacles encountered in targeting antigens that display low copy numbers on cancer cells by increasing the number of the constituent antibodies of a homodimeric antibody in proximity to and/or engaged with the cancer cells. Homodimeric antibodies may, therefore, be ideal for targeting cancers that display a low expression density of a cell surface antigen. In the case of an immunoconjugate, for example, homodimeric antibodies are about twice the size of monomeric antibodies and can therefore carry about twice the payload as monomeric antibodies to increase potency. When homodimeric antibodies are engineered for Fc-receptor mediated cytotoxicity, then a single antigen-binding event positions twice as many Fc regions in proximity to a target cell as a monomeric antibody.

The preceding Background and Summary sections are provided as a brief introduction to the described subject matter as well as a synopsis of some of the technological improvements and advantages that it provides. The Background and Summary shall not be construed as identifying essential aspects of the described subject matter, nor shall they be construed to limit the interpretation of this specification or any patent claim that matures from this specification.

BRIEF DESCRIPTION OF THE DRAWINGS

A further understanding of this specification may be appreciated with reference to the following drawings. The drawings are exemplary, and neither this specification nor any patent claim that matures from this specification shall be construed as limited by the drawings.

DETAILED DESCRIPTION

Figure 1:
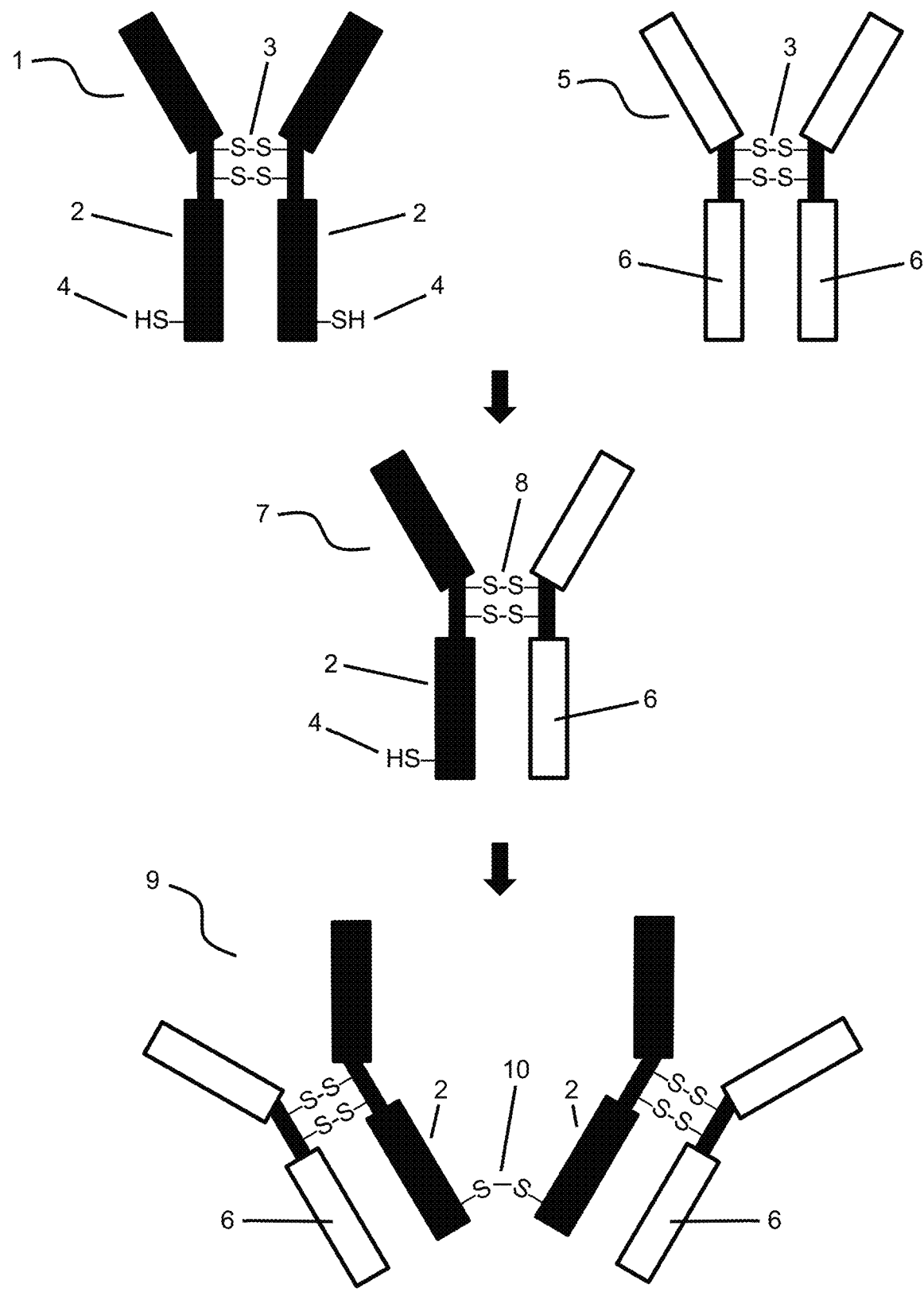
FIG. 1 is a drawing that depicts a general method to produce a homodimeric antibody, in which a single disulfide bond crosslinks two different IgG antibodies.

Various aspects of this disclosure relate to a method to treat cancer in a human subject, comprising administering a therapeutically effective amount of an immunotherapeutic to the subject, wherein the immunotherapeutic is a homodimeric antibody that is optionally conjugated to a radioactive isotope or pharmaceutical agent.

The term "antibody" includes immunoglobulins (Ig's) of different classes (for example, IgA, IgG, IgM, IgD, and IgE) and subclasses (for example, IgG2a and IgG4) and also includes fully-human antibodies, chimeric human/animal antibodies (such as human/mouse antibodies), and engineered variants thereof. This specification describes, for example, a chimeric human-mouse IgG (chAB2) as well as a fully-human IgG4 (SP17-AB2) that was engineered to contain a S228P mutation and a fully-human IgG1. The homodimeric antibodies of this disclosure typically comprise IgG antibodies.

The term "chimeric human/animal antibody" uses the term "chimeric" as conventionally used in relation to the term "antibody" in the field of immunology, which is different from the term "chimeric antibody" as the terms are used in this disclosure. In this disclosure, the term "chimeric antibody" refers to an IgG antibody that has one or both of (1) two heavy chains that comprise two different amino acid sequences and (2) two light chains that comprise two different amino acid sequences. Methods of producing such chimeric antibodies are described, for example, in U.S. Pat. Nos. 9,862,769 B2 and 10,344,050 B2, which are incorporated by reference in their entireties. These methods, which are branded as the DuoBody® platform (Genmab, Denmark), were developed to manufacture bispecific antibodies that bind two different antigens. While the chimeric antibodies of this disclosure may optionally bind two different antigens, the novelty and advantages of this disclosure arise from a cysteine mutation that is present on only a single chain of a chimeric antibody, which allows for the chimeric antibody to form a single disulfide bond.

The heavy chains or light chains of a chimeric antibody have two different amino acid sequences at least because either one of the heavy chains or one of the light chains includes a cysteine mutation to allow for the single disulfide bond. U.S. Pat. Nos. 9,862,769 B2 and 10,344,050 B2 also describe additional mutations that favor separation of the heavy chains of an IgG such as F405L and K409R mutations to IgG1s. Such additional mutations, however, are not required to engineer chimeric antibodies. The additional mutations instead simply increase relative yields. The amino acid sequences may also vary, for example, either to manufacture dimers of bispecific antibodies, as an artifact from cloning, or for other reasons that do not limit this disclosure.

In this disclosure, the amino acid positions of an IgG are defined according to EU numbering as set forth in Kabat, E. A. et al., "Sequences of proteins of immunological interest." 5th Edition—US Department of Health and Human Services, NIH publication No. 91-3242 (1991) (hereinafter, "Kabat"), which is incorporated by reference in its entirety.

Many strategies exist for preparing homodimeric antibodies, and the precise linking strategy shall not limit this disclosure or any claim that matures from this disclosure. A first portion of an IgG antibody may be combined, for example, with a molar excess of sulfosuccinimidyl 4-(N-maleimidomethyl)cyclohexane-1-carboxylate (sulfo-SMCC) or succinimidyl 4-(N-maleimidomethyl)cyclohexane-1-carboxylate (SMCC) to modify one or more amines of the antibody (such as an epsilon-amino group of a lysine) with a thiol-reactive maleimide. This conjugation strategy is generally compatible with antibodies and is used, for example, to crosslink mertansine to trastuzumab to create the antibody-drug conjugate trastuzumab emtansine, which is also known as Kadcyla®. A second portion of the IgG antibody may be combined, for example, with a molar excess of N-succinimidyl S-acetylthiopropionate (SATP) or N-succinimidyl S-acetylthioacetate (SATA), for example, to modify one or more amines of the antibody (such as an epsilon-amino group of a lysine) with an acetyl-protected thiol. The thiol may then be deprotected, for example, under acidic conditions with hydroxylamine. An approximately equimolar amount of the first portion and second portion of the IgG antibody may then be crosslinked. The resultant homodimeric antibody may be purified, for example, by dialysis and/or size-exclusion chromatography.

IgG antibodies contain dozens of lysine residues, and thus, chemical crosslinking based upon a strategy that modifies primarily epsilon-amino groups of lysines will generally result in a heterogenous mixture of various different homodimers that display various different efficacies. Precise quaternary structure may be enforced, for example, by cloning thiols into specific positions within an antibody. Such strategies are known and described, for example, in Shopes, B., "A genetically engineered human IgG mutant with enhanced cytolytic activity," J. IMMUNOL. 1992 148(9): 2918-22. A novel crosslinking strategy is depicted in FIG. 1 and described further below.

FIG. 1 depicts an exemplary strategy to crosslink two IgG antibodies with a disulfide bond, which is further described in Example 4 below; this strategy nevertheless shall not limit this disclosure or any patent claim that matures from this disclosure. A first IgG 1 is provided, which comprises two half molecules 2 that each comprise a heavy chain and a light chain. The amino acid sequence of the heavy chain is the same for each half molecule 2, and the amino acid sequence of the light chain is the same for each half molecule 2. The two half molecules 2 are crosslinked with disulfide bonds 3, which occur at the hinge regions of the first IgG 1. Each half molecule 2 comprises a mutation of a native amino acid to cysteine 4, which may occur in either the heavy chains or the light chains. The first IgG 1 comprises two such cysteine mutations 4, which are depicted as present on the heavy chains.

A second IgG 5 is also provided, which comprises two half molecules 6 that each comprise a heavy chain and a light chain. The amino acid sequence of the heavy chain is the same for each half molecule 6, and the amino acid sequence of the light chain is the same for each half molecule 6. The two half molecules 6 are crosslinked with disulfide bonds 3, which occur at the hinge regions of the second IgG 5. Each half molecule 6 lacks the mutation of the native amino acid to cysteine.

The first IgG 1 and the second IgG 5 are combined under mild reducing conditions, such as in the presence of cysteamine, to reduce the disulfide bonds 3 without reducing other disulfide bonds of the first IgG 1 and the second IgG 5. Other disulfide bonds include disulfide bonds that covalently attach the light chains to the heavy chains and disulfide bonds that enforce tertiary structure. Non-limiting examples of suitable reducing agents include cysteamine.

Following reduction of the disulfide bonds 3, the half molecules 2 of the first IgG 1 may dissociate, the half molecules 6 of the second IgG 5 may dissociate, and a half molecule 2 of the first IgG 1 may then pair with a half molecule 6 of the second IgG 5. Various mutations such as F405L and K409R (as described herein when the first IgG 1 and the second IgG 5 are IgG1s) may favor one or both of dissociation of two half molecules 2, 6 of the first IgG 1 and/or the second IgG 5 and the pairing of a half molecule 2 of the first IgG 1 with a half molecule 6 of the second IgG 5.

After incubating the first IgG 1 and the second IgG 5 under reducing conditions that allow for the two half molecules 2, 6 of the first IgG 1 and the second IgG 5 to dissociate and then pair, the paired half molecules 2,6 of the first IgG 1 and the second IgG 5 are oxidized to form disulfide bonds 8 that crosslink the half molecule 2 of the first IgG 1 to the half molecule 6 of the second IgG 5 and result in a chimeric immunotherapeutic 7. The chimeric immunotherapeutic 7 contains a single half molecule 2 of the first IgG 1 such that the chimeric immunotherapeutic 7 comprises a single mutation of a native amino acid to cysteine 4.

After incubating the first IgG 1 and the second IgG 5 under reducing conditions that allow for the two half molecules 2, 6 of the first IgG 1 and the second IgG 5 to dissociate and then pair, the cysteines 4 of two different chimeric immunotherapeutics 7 are oxidized to form a disulfide bond 10 that crosslinks the two different chimeric immunotherapeutics 7 to form a homodimeric antibody 9.

FIG. 1 depicts the disulfide bonds 8 of the chimeric immunotherapeutic 7 forming prior to the disulfide bond 10 that crosslinks the two different chimeric immunotherapeutics 7 to form the homodimeric antibody 9, and these disulfide bonds 8 likely form prior to the disulfide bond 10 that crosslinks the two different chimeric immunotherapeutics 7, for example, due to proximity enforced by noncovalent interactions between the half molecules 2, 6 of the first IgG 1 and the second IgG 5. The order depicted in FIG. 1 nevertheless shall not limit this disclosure or any patent claim that matures from this disclosure, for example, as the disulfide bond 10 that crosslinks the two different chimeric immunotherapeutics 7 may form either contemporaneously with the disulfide bonds 8 that crosslink the half molecules 2,6 of the first IgG 1 and the second IgG 5 or even prior to formation of these disulfide bonds 8.

Two IgG antibodies of a homodimeric antibody are not necessarily identical and may vary, for example, in post-translational modifications that generally result in heterogeneous glycosylation patterns. In some embodiments, the two IgG antibodies of a homodimeric antibody are encoded by the same nucleotide sequence(s), and such IgG antibodies generally have the same amino acid sequences. In some embodiments, the two IgG antibodies of a homodimeric antibody are encoded by different nucleotide sequences and encode different amino acid sequences, which different amino acid sequences may, for example, enforce a specific quaternary structure such as with one or more of inter-IgG disulfide bond(s), complementary sterics, and complementary electrostatic charges to facilitate favorable orientations between the two IgG antibodies that allow for improved avidity relative to random or otherwise un-optimized orientations. In all embodiments, the primary amino acid sequences of the variable domains of the two IgG antibodies of a homodimeric antibody are the same.

The term "cancer" refers to carcinomas, sarcomas, lymphomas, leukemias, germ cell tumors, and blastomas of any type. In some embodiments, the cancer is brain cancer, ovarian cancer, breast cancer, vaginal cancer, vulvar cancer, uterine cancer, cervical cancer, endometrial cancer, prostate cancer, testicular cancer, penile cancer, liver cancer, intrahepatic bile duct cancer, lung cancer, small cell lung cancer, non-small cell lung cancer, bronchial cancer, mesothelioma, pancreatic cancer, gall bladder cancer, non-melanoma skin cancer, melanoma, Kaposi sarcoma, thyroid cancer, head and neck cancer, nasopharyngeal cancer, oropharyngeal cancer, hypopharyngeal cancer, laryngeal cancer, oral cavity cancer, tongue cancer, mouth cancer, salivary gland cancer, esophageal cancer, gastric cancer, colorectal cancer, colon cancer, rectal cancer, anal cancer, kidney cancer, renal cell cancer, renal pelvis cancer, bladder cancer, urethral cancer, Hodgkin lymphoma, non-Hodgkin's lymphoma, myeloma, multiple myeloma, acute lymphocytic leukemia, chronic lymphocytic leukemia, acute myeloid leukemia, chronic myeloid leukemia, osteosarcoma, or soft tissue cancer. In some specific embodiments, the cancer is multiple myeloma, ovarian cancer, or non-small cell lung cancer.

The term "treat" refers to at least one of: to cure a cancer; to increase the probability that a cancer will be cured; to shorten the time over which a cancer is cured; to increase the probability that the time necessary to cure a cancer will be shortened; to decrease the severity of a cancer; to increase the probability that the severity of a cancer will decrease; to shorten the time over which the severity of a cancer is decreased; to increase the probability that the time necessary to decrease the severity of a cancer will be shortened; to inhibit a cancer from worsening; to increase the probability that a cancer will not worsen; to delay the worsening of a cancer; to increase the probability that the worsening of a cancer will be delayed; to inhibit the occurrence or recurrence of a cancer; to decrease the probability that a cancer will occur or reoccur; to delay the onset of a cancer; to increase the probability that the onset of a cancer will be delayed; to alleviate at least one symptom of a cancer; to increase the probability that at least one symptom of a cancer will be alleviated; to shorten the time over which at least one symptom of a cancer is alleviated; to increase the probability that the time necessary to alleviate at least one symptom of a cancer will be shortened; to decrease the severity of at least one symptom of a cancer; to increase the probability that the severity of at least one symptom of a cancer will be decreased; to shorten the time over which the severity of at least one symptom of a cancer is decreased; to increase the probability that the time necessary to decrease the severity of at least one symptom of a cancer will be shortened; to inhibit at least one symptom of a cancer from worsening; to increase the probability that at least one symptom of a cancer will not worsen; to delay the worsening of at least one symptom of a cancer; to increase the probability that the worsening of at least one symptom of a cancer will be delayed; to inhibit at least one symptom of a cancer from occurring or reoccurring; to decrease the probability that at least one symptom of a cancer will occur or reoccur; to delay the onset of at least one symptom of a cancer; and to increase the probability that the onset of at least one symptom of a cancer will be delayed.

In some embodiments, the administering is performed by injection. In some specific embodiments, the injection is an intravenous injection, intradermal injection, subcutaneous injection, intramuscular injection, intraperitoneal injection, or intratumoral injection. In some very specific embodiments, the injection is an intravenous injection.

The term "therapeutically effective amount" is an amount that is effective to treat cancer, which amount is generally first-determined empirically based upon pre-clinical data and then confirmed by performing pilot and/or phase I-II clinical trials.

In some embodiments, the immunotherapeutic comprises a homodimeric antibody and either a radioisotope or a labile pharmaceutical agent.

In some embodiments, the homodimeric antibody comprises two IgG antibodies that are covalently crosslinked, and each IgG antibody comprises two antigen-binding sites that each specifically bind a cancer-associated antigen such that the homodimeric antibody comprises exactly four antigen-binding sites that each specifically bind the cancer-associated antigen.

In some embodiments, each of the two IgG antibodies has at least 95 percent amino acid sequence identity with a therapeutic antibody selected from 3F8, abagovomab, abituzumab, adecatumumab, amatuximab, andecaliximab, anrukinzumab, apolizumab, ascrinvacumab, atezolizumab, avelumab, basiliximab, bavituximab, belimumab, bemarituzumab, bermekimab, bevacizumab, bivatuzumab, bleselumab, blontuvetmab, brontictuzumab, cabiralizumab, camrelizumab, capromab, carotuximab, cemiplimab, cetrelimab, cetuximab, cibisatamab, cirmtuzumab, cixutumumab, clazakizumab, codrituzumab, conatumumab, cusatuzumab, dacetuzumab, daclizumab, dalotuzumab, daratumumab, dectrekumab, demcizumab, detumomab, dinutuximab, dinutuximab beta, dostarlimab, drozitumab, duligotuzumab, durvalumab, dusigitumab, ecromeximab, edrecolomab, eldelumab, elgemtumab, elotuzumab, elsilimomab, emactuzumab, emibetuzumab, enavatuzumab, enoblituzumab, enoticumab, ensituximab, epratuzumab, etaracizumab, etigilimab, faricimab, farletuzumab, fibatuzumab, ficlatuzumab, figitumumab, flanvotumab, fresolimumab, futuximab, galiximab, ganitumab, gatipotuzumab, gevokizumab, gilvetmab, gimsilumab, girentuximab, gomiliximab, icrucumab, ifabotuzumab, imalumab, imaprelimab, imgatuzumab, inebilizumab, inolimomab, intetumumab, ipilimumab, iratumumab, isatuximab, iscalimab, istiratumab, labetuzumab, lacnotuzumab, lebrikizumab, lenzilumab, leronlimab, lexatumumab, lintuzumab, lirilumab, lucatumumab, lulizumab pegol, lumiliximab, lumretuzumab, lutikizumab, mapatumumab, margetuximab, matuzumab, milatuzumab, mitumomab, modotuximab, mogamulizumab, monalizumab, namilumab, narnatumab, navicixizumab, naxitamab, necitumumab, nesvacumab, nimotuzumab, nivolumab, obinutuzumab, ocaratuzumab, ocrelizumab, ofatumumab, olaratumab, oleclumab, olokizumab, omburtamab, ontuxizumab, oregovomab, otlertuzumab, panitumumab, pankomab, parsatuzumab, pasotuxizumab, patritumab, pembrolizumab, pemtumomab, pertuzumab, pidilizumab, pritumumab, prolgolimab, racotumomab, radretumab, ramucirumab, ravagalimab, relatlimab, retifanlimab, rilotumumab, rinucumab, rituximab, robatumumab, romilkimab, rosmantuzumab, samalizumab, sarilumab, selicrelumab, seribantumab, sibrotuzumab, siltuximab, sintilimab, sirukumab, spartalizumab, tabalumab, tafasitamab, talacotuzumab, tarextumab, tavolimab, telisotuzumab, tenatumomab, teneliximab, tepoditamab, teprotumumab, theralizumab, tigatuzumab, timigutuzumab, tiragotumab, tislelizumab, tomuzotuximab, tositumomab, tovetumab, tralokinumab, trastuzumab, tremelimumab, ublituximab, ulocuplumab, urelumab, utomilumab, vanalimab, vantictumab, vanucizumab, varisacumab, varlilumab, veltuzumab, volociximab, vonlerolizumab, votumumab, xentuzumab, zalutumumab, zatuximab, zenocutuzumab, and zolbetuximab. In some specific embodiments, a first IgG of the two IgG antibodies has at least 98 percent amino acid sequence identity with the therapeutic antibody. In some very specific embodiments, the first IgG has at least 99 percent amino acid sequence identity with the therapeutic antibody. The first IgG may lack 100 percent amino acid sequence identity with the therapeutic antibody because the first IgG comprises a mutation of a native amino acid to a cysteine (such as either S444C or S 119C) to allow for a disulfide bond that crosslinks chimeric IgGs of a dimeric immunotherapeutic. The first IgG may also lack 100 percent amino acid sequence identity with the therapeutic antibody, for example, to introduce one or more mutations that favor dissociation of half molecules of the first IgG (such as either F405L or K409R). The first IgG may also lack 100 percent amino acid sequence identity with the therapeutic antibody, for example, to remove or alter glycosylation sites, to modulate effector function, to modulate half-life in vivo, to improve stability, to reduce antigenicity in vivo, as an artifact of cloning, and/or for any number of other reasons.

In some embodiments, the first IgG has at least 95 percent amino acid sequence with a therapeutic antibody set forth in the preceding paragraph, and the second IgG has at least 95 percent amino acid sequence identity with the same therapeutic antibody. In some specific embodiments, the first IgG has at least 98 percent amino acid sequence with a therapeutic antibody set forth in the preceding paragraph, and the second IgG has at least 98 percent amino acid sequence identity with the same therapeutic antibody. In some very specific embodiments, the first IgG has at least 99 percent amino acid sequence with a therapeutic antibody set forth in the preceding paragraph, and the second IgG has at least 99 percent amino acid sequence identity with the same therapeutic antibody.

In some embodiments, the homodimeric antibody is a homodimer of 3F8, abagovomab, abituzumab, adecatumumab, amatuximab, andecaliximab, anrukinzumab, apolizumab, ascrinvacumab, atezolizumab, avelumab, basiliximab, bavituximab, belimumab, bemarituzumab, bermekimab, bevacizumab, bivatuzumab, bleselumab, blontuvetmab, brontictuzumab, cabiralizumab, camrelizumab, capromab, carotuximab, cemiplimab, cetrelimab, cetuximab, cibisatamab, cirmtuzumab, cixutumumab, clazakizumab, codrituzumab, conatumumab, cusatuzumab, dacetuzumab, daclizumab, dalotuzumab, daratumumab, dectrekumab, demcizumab, detumomab, dinutuximab, dinutuximab beta, dostarlimab, drozitumab, duligotuzumab, durvalumab, dusigitumab, ecromeximab, edrecolomab, eldelumab, elgemtumab, elotuzumab, elsilimomab, emactuzumab, emibetuzumab, enavatuzumab, enoblituzumab, enoticumab, ensituximab, epratuzumab, etaracizumab, etigilimab, faricimab, farletuzumab, fibatuzumab, ficlatuzumab, figitumumab, flanvotumab, fresolimumab, futuximab, galiximab, ganitumab, gatipotuzumab, gevokizumab, gilvetmab, gimsilumab, girentuximab, gomiliximab, icrucumab, ifabotuzumab, imalumab, imaprelimab, imgatuzumab, inebilizumab, inolimomab, intetumumab, ipilimumab, iratumumab, isatuximab, iscalimab, istiratumab, labetuzumab, lacnotuzumab, lebrikizumab, lenzilumab, leronlimab, lexatumumab, lintuzumab, lirilumab, lucatumumab, lulizumab pegol, lumiliximab, lumretuzumab, lutikizumab, mapatumumab, margetuximab, matuzumab, milatuzumab, mitumomab, modotuximab, mogamulizumab, monalizumab, namilumab, narnatumab, navicixizumab, naxitamab, necitumumab, nesvacumab, nimotuzumab, nivolumab, 20acituzumab20, ocaratuzumab, ocrelizumab, ofatumumab, olaratumab, oleclumab, olokizumab, omburtamab, ontuxizumab, oregovomab, otlertuzumab, panitumumab, pankomab, parsatuzumab, pasotuxizumab, patritumab, pembrolizumab, pemtumomab, pertuzumab, pidilizumab, pritumumab, prolgolimab, racotumomab, radretumab, ramucirumab, ravagalimab, relatlimab, retifanlimab, rilotumumab, rinucumab, rituximab, robatumumab, romilkimab, rosmantuzumab, samalizumab, sarilumab, selicrelumab, seribantumab, sibrotuzumab, siltuximab, sintilimab, sirukumab, spartalizumab, tabalumab, tafasitamab, talacotuzumab, tarextumab, tavolimab, telisotuzumab, tenatumomab, teneliximab, tepoditamab, teprotumumab, theralizumab, tigatuzumab, timigutuzumab, tiragotumab, tislelizumab, tomuzotuximab, tositumomab, tovetumab, tralokinumab, trastuzumab, tremelimumab, ublituximab, ulocuplumab, urelumab, utomilumab, vanalimab, vantictumab, vanucizumab, varisacumab, varlilumab, veltuzumab, volociximab, vonlerolizumab, votumumab, xentuzumab, zalutumumab, zatuximab, zenocutuzumab, or zolbetuximab. Homodimeric versions of the foregoing antibodies may be manufactured, for example, with the SATP/SATA and sulfo-SMCC/SMCC cross-linking strategy as described herein.

In some embodiments, the homodimeric antibody comprises two bispecific IgG antibodies that are covalently crosslinked, and each IgG antibody comprises two antigen-binding sites that each specifically bind a different cancer-associated antigen such that the homodimeric antibody comprises exactly four antigen-binding sites that each specifically bind one of two different cancer-associated antigen. In some specific embodiments, the homodimeric antibody is a homodimer of amivantamab, glofitamab, talquetamab, or teclistamab, which are each bispecific antibodies.

In some embodiments, the cancer-associated antigen is 4-1BB, 5'-nucleotidase, 5T4, activin receptor-like kinase 1, alpha-fetoprotein, angiopoietin 2, AXL, B7-H3, B-cell activating factor (BAFF), B-cell maturation antigen (BCMA), B-cell receptor (BCR), c-Met, C242, CA-125, CanAg, carbonic anhydrase 9 (CA-IX), carcinoembryonic antigen, CCR4, CCR5, CD3, CD4, CD19, CD20, CD22, CD23, CD25, CD27, CD28, CD30, CD33, CD37, CD38, CD40, CD44, CD51, CD56, CD70, CD74, CD79B, CD80, CD123, CD134, CD152, CD200, CD276, CD319, CEACAM5, claudin 18, coagulation factor III, connective tissue growth factor (CTGF), colony stimulating factor 1 (CSF1), colony stimulating factor 1 receptor (CSF1R), colony stimulating factor 2 (CSF2), CTLA-4, CXCR4, dendritic cell-associated lectin 2, DLL3, DLL4, DR5, EGFL7, EGFR, endoglin, EpCAM, ephrin receptor A3 (EPHA3), epidermal growth factor receptor (EGFR), ERBB3 (HER3), ERB4, fibroblast activation protein alpha (FAP), FGFR2, fibronectin extra domain-B, folate hydrolase, folate receptor 1, Frizzled receptor, GD2 ganglioside, GD3 ganglioside, gelatinase B, glycoprotein 100 (gp100), glypican 3, GPNMB, G protein-coupled receptor 5D (GPRC5D), GUCY2C, hepatocyte growth factor (HGF), HER1, HER2, HGFR, histone complex, HLA-DR, human scatter factor receptor kinase, IGF-1 receptor (IGF-1R; CD221), IGF-2, interleukin 1alpha, interleukin-2, interleukin-6, interleukin-13, integrin alph5beta1, integrin alphaVbeta3, KIR2D, LAG3, Lewis-Y antigen, LIV-1, LRRC15, macrophage migration inhibitory factor (MIF), MCP-1, melanoma cell adhesion molecule (MCAM), mesothelin, MUC1, MUC5AC, nectin-4, NGNA ganglioside, Notch 1, Notch receptor, NRP1, PCDC1, PD-1, PD-L1, PDGFRA, phosphate-sodium co-transporter, phosphatidylserine, PTK7, root plate-specific spondin 3, ROR1, SDC1, SLAMF7, SLITRK6, Sp17, STEAP1, syndecan 1, TEM1, tenascin C, TGF-beta, TIGIT, TRAIL-R1, TRAIL-R2, tumor-associated calcium signal transducer 2 (TROP-2), tumor antigen CTAA16.88, tumor-specific glycosylated MUC1, tumor-associated glycoprotein 72 (TAG-72), TWEAK receptor, TYRP1, VEGF-A, VEGFR-1, VEGFR-2, or vimentin. In some specific embodiments, the cancer-associated antigen is Sp17.

In some embodiments, the method comprises administering a therapeutically effective amount of an immunotherapeutic to the subject, wherein: (1) the immunotherapeutic comprises a homodimeric antibody and either a radioisotope or a labile pharmaceutical agent; (2) the homodimeric antibody comprises two IgG antibodies that are covalently crosslinked; and (3) each IgG antibody comprises two antigen-binding sites that each specifically bind a cancer-associated antigen such that the homodimeric antibody comprises exactly four antigen-binding sites that each specifically bind the cancer-associated antigen.

Various aspects of this disclosure relate to a method to treat cancer in a human subject, comprising administering to the subject a therapeutically effective amount of an immunotherapeutic, wherein (1) the cancer comprises cells that express Sp17; (2) the immunotherapeutic comprises a homodimeric antibody that comprises two IgG antibodies that are covalently crosslinked; and (3) each IgG antibody comprises two antigen-binding sites that each specifically bind Sp17 such that the homodimeric antibody comprises exactly four antigen-binding sites that each specifically bind Sp17.

In some embodiments, the immunotherapeutic is an immunoconjugate, and the homodimeric antibody is conjugated to a radioactive isotope. In some specific embodiments, the radioactive isotope is actinium-225, astatine-211, bismuth-212, bismuth-213, copper-67, gallium-68, holmium-166, indium-111, iodine-124, iodine-131, lutetium-177, samarium-153, technetium-99, terbium-149, or yttrium-90. In some very specific embodiments, the radioactive isotope is indium-111, iodine-124, iodine-131, lutetium-177, or yttrium-90.

In some embodiments, the homodimeric antibody is a homodimer of 3F8, clivatuzumab tetraxetan, derlotuximab biotin, ibritumomab tiuxetan, lilotomab satetraxetan, tacatuzumab tetraxetan, or tositumomab, each of which are immunoconjugates. Homodimeric versions of the foregoing antibodies may be manufactured, for example, with the SATP/SATA and sulfo-SMCC/SMCC cross-linking strategy as described herein.

Examples of antibodies conjugated to radioactive isotopes include tositumomab (also known as BEXXAR®) and ibritumomab tiuxetan (also known as ZEVALIN®). Those of ordinary skill are capable of designing antibodies that are conjugated to radioactive isotopes using known strategies such as those used to conjugate iodine-131 in tositumomab and to conjugate yittrium-90 or indium-111 to ibritumomab (see, for example, U.S. Pat. No. 6,565,827 & 7,422,739, which are incorporated by reference in their entirety).

In some embodiments, the immunotherapeutic is an immunoconjugate, and the homodimeric antibody is conjugated to a pharmaceutical agent. In some specific embodiments, the homodimeric antibody is conjugated to a moiety selected from a calicheamicin, camptothecin, deruxtecan, doxorubicin, emtansine, exatecan, irinotecan, maleimidocaproyl monomethyl auristatin F, mertansine (DM1), monomethyl auristatin F, paclitaxel, PE38, pyrrolobenzodiazepine, SN-38, and vedotin.

In some embodiments, the homodimeric antibody is a homodimer of anetumab ravtansine, aprutumab ixadotin, azintuxizumab vedotin, belantamab mafodotin, brentuximab vedotin, camidanlumab tesirine, cantuzumab mertansine, cantuzumab ravtansine, cbr96-doxorubicin immunoconjugate, cofetuzumab pelidotin, coltuximab ravtansine, denintuzumab mafodotin, depatuxizumab mafodotin, enapotamab vedotin, enfortumab vedotin, gemtuzumab ozogamicin, glembatumumab vedotin, iladatuzumab vedotin, indatuximab ravtansine, indusatumab vedotin, inotuzumab ozogamicin, ladiratuzumab vedotin, laprituximab emtansine, lifastuzumab vedotin, loncastuximab tesirine, lorvotuzumab mertansine, losatuximab vedotin, mirvetuximab soravtansine, moxetumomab pasudotox, naratuximab emtansine, pinatuzumab vedotin, polatuzumab vedotin, rovalpituzumab tesirine, sacituzumab govitecan, samrotamab vedotin, sirtratumab vedotin, sofituzumab vedotin, taplitumomab paptox, telisotuzumab vedotin, tisotumab vedotin, trastuzumab duocarmazine, trastuzumab emtansine, vadastuximab talirine, vandortuzumab vedotin, vorsetuzumab mafodotin, or trastuzumab deruxtecan, each of which are antibody-drug conjugates. Homodimeric versions of the foregoing antibodies may be manufactured, for example, with the SATP/SATA and sulfo-SMCC/SMCC cross-linking strategy as described herein.

Examples of antibodies conjugated to pharmaceutical agents include gemtuzumab ozogamicin (also known as MYLOTARG®) and trastuzumab emtansine (also known as KADCYLA®). Those of ordinary skill are capable of designing antibodies that are conjugated to pharmaceutical agents using known strategies such as those used to conjugate calicheamicin to gemtuzumab and emtansine to trastuzumab (see, for example, U.S. Pat. No. 5,877,296 & 8,088,387, which are incorporated by reference in their entirety).

In some embodiments, a monomeric antibody that consists of the IgG antibody has a reference efficacy against the cancer; the immunotherapeutic has an improved efficacy against the cancer; the reference efficacy and the improved efficacy are determined by an in vitro cytotoxicity assay on cells that express the cancer-associated antigen; and the improved efficacy is more than 100 percent more effective per mole than the reference efficacy. The in vitro cytotoxicity assay may measure cytotoxicity against cancer cells such as an immortalized cell line of the cancer cells, which cytotoxicity is optionally mediated by leukocytes of the in vitro cytotoxicity assay. The leukocytes may be, for example, NK-92 cells that are modified to express the Fc receptor.

In some embodiments, the homodimeric antibody is conjugated to a radioactive isotope or pharmaceutical agent; a monomeric antibody has a reference efficacy against the cancer; the immunotherapeutic has an improved efficacy against the cancer; the monomeric antibody consists of (1) the IgG antibody, (2) the radioactive isotope or pharmaceutical agent, and (3) a linker that links the radioactive isotope or pharmaceutical agent to the IgG antibody; the reference efficacy and the improved efficacy are determined by an in vitro cytotoxicity assay on cells that express the cancer-associated antigen; and the improved efficacy is more than 100 percent more effective per mole than the reference efficacy. The in vitro cytotoxicity assay may measure cytotoxicity against cancer cells such as an immortalized cell line of the cancer cells.

In some embodiments, a monomeric antibody that consists of the IgG antibody has a reference efficacy against the cancer; the immunotherapeutic has an improved efficacy against the cancer; the reference efficacy and the improved efficacy are determined by one or more clinical trials; and the improved efficacy is more than 100 percent more effective per mole than the reference efficacy. In some specific embodiments, efficacy is determined by overall survival. In some specific embodiments, efficacy is determined by progression-free survival.

In some embodiments, the homodimeric antibody is conjugated to a radioactive isotope or pharmaceutical agent; a monomeric antibody has a reference efficacy against the cancer; the monomeric antibody consists of (1) the IgG antibody, (2) the radioactive isotope or pharmaceutical agent, and (3) a linker that links the radioactive isotope or pharmaceutical agent to the IgG antibody; the immunotherapeutic has an improved efficacy against the cancer; the reference efficacy and the improved efficacy are determined by one or more clinical trials; and the improved efficacy is more than 100 percent more effective per mole than the reference efficacy. In some specific embodiments, efficacy is determined by overall survival. In some specific embodiments, efficacy is determined by progression-free survival.

In some embodiments, the improved efficacy is more than 150 percent more effective per mole than the reference efficacy. In some specific embodiments, the improved efficacy is more than 200 percent more effective per mole than the reference efficacy.

In some embodiments, a monomeric antibody that consists of the IgG antibody has a reference infusion time, which is an amount of time necessary to infuse an effective amount of the monomeric antibody to treat the cancer; the immunotherapeutic has a shorter infusion time, which is an amount of time necessary to infuse the effective amount of the immunotherapeutic to treat the cancer; and the shorter infusion time is at least 30 minutes shorter than the reference infusion time (such as at least one hour shorter). In some specific embodiments, the shorter infusion time is shorter than the reference infusion time because the immunotherapeutic has a superior efficacy relative to the monomeric antibody. In some very specific embodiments, the shorter infusion time is shorter than the reference infusion time because the immunotherapeutic has a superior efficacy per mole relative to the monomeric antibody. In some specific embodiments, the shorter infusion time is shorter than the reference infusion time because formulations comprising the immunotherapeutic have a greater mass/volume concentration relative to formulations comprising the monomeric antibody. Immunotherapeutics of this disclosure such as homodimeric IgG antibodies may allow for increased mass/volume concentrations relative to monomeric IgG antibodies, for example, because homodimeric IgG antibodies have molecular weights that are approximately double that of monomeric IgG antibodies.

In some embodiments, the homodimeric antibody is conjugated to a radioactive isotope or pharmaceutical agent; a monomeric antibody has a reference infusion time, which is an amount of time necessary to infuse an effective amount of the monomeric antibody to treat the cancer; the monomeric antibody consists of (1) the IgG antibody, (2) the radioactive isotope or pharmaceutical agent, and (3) a linker that links the radioactive isotope or pharmaceutical agent to the IgG antibody; the immunotherapeutic has a shorter infusion time, which is an amount of time necessary to infuse the effective amount of the immunotherapeutic to treat the cancer; and the shorter infusion time is at least 30 minutes shorter than the reference infusion time (such as at least one hour shorter). In some specific embodiments, the shorter infusion time is shorter than the reference infusion time because the immunotherapeutic has a superior efficacy relative to the monomeric antibody. In some very specific embodiments, the shorter infusion time is shorter than the reference infusion time because the immunotherapeutic has a superior efficacy per mole relative to the monomeric antibody. In some specific embodiments, the shorter infusion time is shorter than the reference infusion time because formulations comprising the immunotherapeutic have a greater mass/volume concentration relative to formulations comprising the monomeric antibody.

In some embodiments, the immunotherapeutic has an infusion time of no greater than 4 hours. In some specific embodiments, the immunotherapeutic has an infusion time of no greater than 3 hours. In some even more specific embodiments, the immunotherapeutic has an infusion time of no greater than 2 hours. In some very specific embodiments, the immunotherapeutic has an infusion time of no greater than 1 hour.

In some embodiments, each antigen-binding site of the IgG antibody comprises (1) a first variable domain that comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; and (2) a second variable domain that comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10. Homodimeric antibodies in which each antigen-binding site comprises the first variable domain and second variable domain as set forth in this paragraph are generally capable of specifically binding Sp17 with high affinity.

In some embodiments, each IgG antibody comprises a heavy chain that has at least 90 percent sequence homology with SEQ ID NO: 11 and a light chain that has at least 90 percent sequence homology with SEQ ID NO: 12. Homodimeric antibodies comprising two IgG antibodies that each comprise a heavy chain and a light chain as set forth in this paragraph are generally capable of specifically binding Sp17 with high affinity.

As used in this disclosure, the term "sequence homology" refers to percent "positives" as determined by Standard Protein BLAST® over the full length of a sequence set forth in a SEQ ID NO. Standard Protein BLAST® is available at https://blast.ncbi.nlm.nih.gov/Blast.cgi?PROGRAM=blastp. BLAST® is generally described in Altschul, et al. (1997), "Gapped BLAST and PSI-BLAST: a new generation of protein database search programs", Nucleic Acids Res. 25:3389-3402, and in Altschul, et al. (2005) "Protein database searches using compositionally adjusted substitution matrices", FEBS J. 272: 5101-5109. As used in this disclosure, the term "sequence identity" refers to the percent of exact matches over the full length of a sequence set forth in a SEQ ID NO.

In some embodiments, the immunotherapeutic comprises a dissociation constant (KD) with the cancer-associated antigen of no greater than 25 nanomolar. In some specific embodiments, the homodimeric antibody has a KD with the cancer-associated antigen of no greater than 10 nanomolar. In some very specific embodiments, the homodimeric antibody has a KD with the cancer-associated antigen of no greater than 2.5 nanomolar. In some embodiments, KD is determined by surface plasmon resonance (such as with a Biacore™ instrument).

In some embodiments, each IgG antibody comprises a human IgG1, IgG2, IgG3, or IgG4 heavy chain constant region and a human kappa or lambda light chain constant region. In some embodiments, each IgG antibody comprises a human IgG1 or IgG4 heavy chain constant region and a human kappa or lambda light chain constant region. In some very specific embodiments, each IgG antibody comprises a human IgG1 or IgG4 heavy chain constant region and a human kappa light chain constant region.

In some embodiments, the two IgG antibodies are covalently crosslinked in the homodimeric antibody with an engineered disulfide bond. S119C and S444C are representative mutations to native amino acids that are known to crosslink IgG1 antibodies with high efficiency. The positions of S119C and S444C are defined according to EU numbering as set forth in Kabat. Other suitable native amino acids may be identified by analyzing crystal structures for IgGs, for example, to identify native amino acids that display solvent-accessible surface areas that are greater than the solvent-accessible surface areas of buried native amino acids. Other suitable native amino acids may include, for example, asparagine amino acids that might otherwise be glycosylated. Other suitable native amino acids may include, for example, (1) alanine amino acids that have a greater solvent-accessible surface area than other alanine amino acids of an IgG, (2) serine amino acids, (3) threonine amino acids, (4) aspartate amino acids, (5) glutamate amino acids, (6) asparagine amino acids, (7) glutamine amino acids, (8) histidine amino acids, (8) arginine amino acids, (9) lysine amino acids, (10) methionine amino acids, and (11) tyrosine amino acids; the scope of suitable native amino acids is nevertheless not limiting and even hydrophobic amino acids may be suitable native amino acids if a hydrophobic amino acid displays a significant solvent-accessible surface area.

In some embodiments, the two IgG antibodies are covalently crosslinked in the homodimeric antibody with a synthetic linker. In the case of sulfo-SMCC- and SATP-mediated cross-linking, for example, the synthetic linker would be 1-oxo-S-{N-[4-formyl-cyclohexyl(methyl)]-3,4-dihydro-2,5-dioxo-1H-pyrrol-3-yl}-3-thiopropyl, wherein the carbon atom of the formyl is covalently bound to a primary amine of a first of the two IgG antibodies and the 1-carbon atom of the propyl is bound to a primary amine of a second of the two IgG antibodies.

Various aspects of this disclosure relate to an immunotherapeutic comprising a homodimeric antibody that comprises two IgG antibodies that are covalently crosslinked, wherein each IgG antibody comprises two antigen-binding sites that each specifically bind Sp17 such that the homodimeric antibody comprises exactly four antigen-binding sites that each specifically bind Sp17.

Various aspects of this disclosure relate to an immunotherapeutic comprising a homodimeric antibody and either a radioisotope or a labile pharmaceutical agent, wherein (1) the homodimeric antibody comprises two IgG antibodies that are covalently crosslinked, and (2) each IgG antibody comprises two antigen-binding sites that each specifically bind a cancer-associated antigen such that the homodimeric immunoconjugate comprises exactly four antigen-binding sites that each specifically bind the cancer-associated antigen.

In some embodiments, the immunotherapeutic is an immunoconjugate, and the homodimeric antibody is conjugated to a radioactive isotope. In some specific embodiments, the radioactive isotope is actinium-225, astatine-211, bismuth-212, bismuth-213, copper-67, gallium-68, holmium-166, indium-111, iodine-124, iodine-131, lutetium-177, samarium-153, technetium-99, terbium-149, or yttrium-90. In some very specific embodiments, the radioactive isotope is indium-111, iodine-124, iodine-131, lutetium-177, or yttrium-90.

In some embodiments, the immunotherapeutic is an immunotherapeutic is an immunoconjugate, and the homodimeric antibody is conjugated to a pharmaceutical agent. In some specific embodiments, the homodimeric antibody is conjugated to a moiety selected from a calicheamicin, camptothecin, deruxtecan, doxorubicin, emtansine, exatecan, irinotecan, maleimidocaproyl monomethyl auristatin F, mertansine, monomethyl auristatin F, paclitaxel, PE38, pyrrolobenzodiazepine, SN-38, and vedotin.

In some embodiments, each antigen-binding site comprises: (1) a first variable domain that comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; and (2) a second variable domain that comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10.

Various aspects of this disclosure relate to homodimeric antibodies that display high-affinity for Sp17. These antibodies were developed using a Fab phage-display biopanning strategy on a library generated from the peripheral blood of 120 healthy donors as set forth in Example 1 below. The library included about a trillion different combinations. The best-performing Fab in the library had an immunoglobulin heavy chain variable region (VH) with the nucleotide sequence set forth in SEQ ID NO: 1 and an immunoglobulin light chain variable region (VL) with the nucleotide sequence set forth in SEQ ID NO: 2, which nucleotide sequences are depicted in Table 1 below. The VH amino acid sequence is set forth in SEQ ID NO: 3, and the VL amino acid sequence is set forth in SEQ ID NO: 4. The VH and VL amino acid sequences are depicted in Table 2 below. CDR sequences are set forth in SEQ ID NO: 5-10 and are independently depicted in Table 3 below. One of ordinary skill will recognize that the precise demarcation between CDR and framework regions is blurred at least for some of the CDRs, and the CDRs as set forth in Table 3 and in SEQ ID NO: 5-10 may therefore include one or more amino acids that might be more-appropriately classified as framework rather than CDR.

Nucleotide sequences encoding the variable regions of the best-performing Fab (SEQ ID NO: 1 & 2) were initially cloned into a mouse IgG2a heavy chain gene and a mouse kappa light chain gene to express a chimeric monoclonal antibody (chAB2). The affinity of the chimeric antibody was determined to be about 2 nanomolar by surface plasmon resonance. Immunohistochemical analysis of the chimeric antibody against 33 normal human tissues indicated that the variable regions lack detectable cross-reactivity.

The human variable regions were then cloned into a human IgG4 heavy chain gene and a human kappa light chain gene to produce a human monoclonal antibody (SP17-AB2) suitable for use as a therapeutic antibody. The heavy chain constant region was mutated to include a S228P mutation to reduce non-specific interactions with Fc receptor gamma (FcTR). The full heavy chain has the amino acid sequence set forth in SEQ ID NO: 10, and the full light chain has the amino acid sequence set forth in SEQ ID NO: 11, which are depicted in Table 4 below.

The human variable regions were then cloned into a human IgG1 heavy chain to produce a human monoclonal antibody suitable for use as a therapeutic antibody. The heavy chain constant region of one clone was mutated to include a S444C mutation to crosslink the IgG1 to form a homodimeric antibody, and an additional mutation F405L was introduced to produce a chimeric antibody as described herein. The heavy chain constant region of a second clone was mutated to include a K409R mutation to produce the chimeric antibody by reducing the hinge regions of the first and second clones to allow half molecules of the first and second clones to recombine as described herein (see, for example, FIG. 1).

Various aspects of this disclosure relate to a homodimeric anti-Sp17 antibody, which comprises the CDRs described above or which comprises sequence homology (or sequence identity) with the VH and VL variable regions that comprise the CDRs as described above.

In all embodiments, each IgG antibody comprises two variable domains. The two variable domains include a heavy chain variable region and a light chain variable region. In some specific embodiments, the heavy chain variable region has a percent sequence homology (or sequence identity) with SEQ ID NO: 5, 6, and 7, and the light chain variable region has a percent sequence homology (or sequence identity) with SEQ ID NO: 8, 9, and 10. In some very specific embodiments, the heavy chain variable region has a percent sequence homology (or sequence identity) with SEQ ID NO: 3, and the light chain variable region has a percent sequence homology (or sequence identity) with SEQ ID NO: 4.

In some embodiments, each IgG antibody comprises (1) a first variable domain that comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; and (2) a second variable domain that comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10.

In some embodiments, each IgG antibody comprises four variable domains, wherein the antibody comprises (1) a third variable domain that comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; and (2) a fourth variable domain that comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10. Such antibodies include, for example, IgG antibodies that bind Sp17.

In some embodiments, one or more of VH CDR1, VH CDR2, VH CDR3, VL CDR1, VL CDR2, and VL CDR3 comprise one or more conservative mutations. Conservative mutations are known in the art and include, for example, threonine to serine, isoleucine to valine or leucine, tyrosine to phenylalanine, aspartate to glutamate, asparagine to glutamine, arginine to lysine, and like substitutions. In this disclosure, a conservative mutation is a "positive" match in Standard Protein BLAST® that is not an identity.

In some embodiments, each IgG antibody comprises two variable domains, wherein: each IgG antibody comprises a first variable domain that comprises an amino acid sequence that has at least 90 percent sequence homology with SEQ ID NO: 3; each IgG antibody comprises a second variable domain that comprises an amino acid sequence that has at least 90 percent sequence homology with SEQ ID NO: 4; and each IgG antibody binds human Sp17. In some specific embodiments, the first variable domain comprises an amino acid sequence that has at least 90 percent sequence identity with SEQ ID NO: 3; the second variable domain comprises an amino acid sequence that has at least 90 percent sequence identity with SEQ ID NO: 4; and the antibody binds human Sp17.

SEQ ID NO: 3 is the VH amino acid sequence, which includes VH CDR1, VH CDR2, VH CDR3, and framework regions. In some embodiments, the VH amino acid sequence comprises mutations relative to SEQ ID NO: 3 such that the VH amino acid sequence has at least 90 percent sequence homology with SEQ ID NO: 3 but less than 100 percent sequence homology. In some specific embodiments, the VH amino acid sequence comprises mutations relative to SEQ ID NO: 3 such that the VH amino acid sequence has at least 90 percent sequence identity with SEQ ID NO: 3 but less than 100 percent sequence identity.

SEQ ID NO: 4 is the VL amino acid sequence, which includes VL CDR1, VL CDR2, VL CDR3, and framework regions. In some embodiments, the VL amino acid sequence comprises mutations relative to SEQ ID NO: 4 such that the VL amino acid sequence has at least 90 percent sequence homology with SEQ ID NO: 4 but less than 100 percent sequence homology. In some specific embodiments, the VL amino acid sequence comprises mutations relative to SEQ ID NO: 4 such that the VL amino acid sequence has at least 90 percent sequence identity with SEQ ID NO: 4 but less than 100 percent sequence identity.

Mutations to the VH and/or VL amino acid sequences may be engineered, for example, to tune the avidity of an antibody to the Sp17 antigen, to modulate expression or glycosylation, and/or for other purposes.

In some embodiments, the first variable domain comprises an amino acid sequence that has at least 95 percent sequence homology with SEQ ID NO: 3. In some specific embodiments, the first variable domain comprises an amino acid sequence that has at least 97 percent sequence homology with SEQ ID NO: 3. In some even more specific embodiments, the first variable domain comprises an amino acid sequence that has at least 98 percent sequence homology with SEQ ID NO: 3. In some very specific embodiments, the first variable domain comprises an amino acid sequence that has at least 99 percent sequence homology with SEQ ID NO: 3.

In some embodiments, the first variable domain comprises an amino acid sequence that has at least 95 percent sequence identity with SEQ ID NO: 3. In some specific embodiments, the first variable domain comprises an amino acid sequence that has at least 97 percent sequence identity with SEQ ID NO: 3. In some even more specific embodiments, the first variable domain comprises an amino acid sequence that has at least 98 percent sequence identity with SEQ ID NO: 3. In some very specific embodiments, the first variable domain comprises an amino acid sequence that has at least 99 percent sequence identity with SEQ ID NO: 3.

In some embodiments, the second variable domain comprises an amino acid sequence that has at least 95 percent sequence homology with SEQ ID NO: 4. In some specific embodiments, the second variable domain comprises an amino acid sequence that has at least 97 percent sequence homology with SEQ ID NO: 4. In some even more specific embodiments, the second variable domain comprises an amino acid sequence that has at least 98 percent sequence homology with SEQ ID NO: 4. In some very specific embodiments, the second variable domain comprises an amino acid sequence that has at least 99 percent sequence homology with SEQ ID NO: 4.

In some embodiments, the second variable domain comprises an amino acid sequence that has at least 95 percent sequence identity with SEQ ID NO: 4. In some specific embodiments, the second variable domain comprises an amino acid sequence that has at least 97 percent sequence identity with SEQ ID NO: 4. In some even more specific embodiments, the second variable domain comprises an amino acid sequence that has at least 98 percent sequence identity with SEQ ID NO: 4. In some very specific embodiments, the second variable domain comprises an amino acid sequence that has at least 99 percent sequence identity with SEQ ID NO: 4.

In some embodiments, each IgG antibody comprises four variable domains, wherein the antibody comprises (1) a third variable domain that comprises an amino acid sequence that has at least 90 percent sequence homology with SEQ ID NO: 3 (such as at least 95, 97, 98, or 99 percent sequence homology); and (2) a fourth variable domain that comprises an amino acid sequence that has at least 90 percent sequence homology with SEQ ID NO: 4 (such as at least 95, 97, 98, or 99 percent sequence homology). In some specific embodiments, the third variable domain comprises an amino acid sequence that has at least 90 percent sequence identity with SEQ ID NO: 3 (such as at least 95, 97, 98, or 99 percent sequence homology), and the fourth variable domain comprises an amino acid sequence that has at least 90 percent sequence identity with SEQ ID NO: 4 (such as at least 95, 97, 98, or 99 percent sequence identity).

In some embodiments, the homodimeric antibody has a KD with human Sp17 of no greater than 25 nanomolar. In some specific embodiments, the homodimeric antibody has a KD with human Sp17 of no greater than 10 nanomolar. In some very specific embodiments, the homodimeric antibody has a KD with human Sp17 of no greater than 2.5 nanomolar.

In some embodiments, each IgG antibody has a heavy chain that has at least 90 percent sequence homology with SEQ ID NO: 11. In some specific embodiments, each IgG antibody has a heavy chain that has at least 95 percent sequence homology with SEQ ID NO: 11. In some even more specific embodiments, each IgG antibody has a heavy chain that has at least 98 percent sequence homology with SEQ ID NO: 11. In some very specific embodiments, each IgG antibody has a heavy chain that has at least 99 percent sequence homology with SEQ ID NO: 11.

In some embodiments, each IgG antibody has a heavy chain that has at least 90 percent sequence identity with SEQ ID NO: 11. In some specific embodiments, each IgG antibody has a heavy chain that has at least 95 percent sequence identity with SEQ ID NO: 11. In some even more specific embodiments, each IgG antibody has a heavy chain that has at least 98 percent sequence identity with SEQ ID NO: 11. In some very specific embodiments, each IgG antibody has a heavy chain that has at least 99 percent sequence identity with SEQ ID NO: 11.

In some embodiments, each IgG antibody has a light chain that has at least 90 percent sequence homology with SEQ ID NO: 12. In some specific embodiments, each IgG antibody has a light chain that has at least 95 percent sequence homology with SEQ ID NO: 12. In some even more specific embodiments, each IgG antibody has a light chain that has at least 98 percent sequence homology with SEQ ID NO: 12. In some very specific embodiments, each IgG antibody has a light chain that has at least 99 percent sequence homology with SEQ ID NO: 12.

In some embodiments, each IgG antibody has a light chain that has at least 90 percent sequence identity with SEQ ID NO: 12. In some specific embodiments, each IgG antibody has a light chain that has at least 95 percent sequence identity with SEQ ID NO: 12. In some even more specific embodiments, each IgG antibody has a light chain that has at least 98 percent sequence identity with SEQ ID NO: 12. In some very specific embodiments, each IgG antibody has a light chain that has at least 99 percent sequence identity with SEQ ID NO: 12.

In some embodiments, each IgG antibody has (1) a heavy chain that has at least 90 percent sequence homology with SEQ ID NO: 11, and (2) a light chain that has at least 90 percent sequence homology with SEQ ID NO: 12. In some specific embodiments, each IgG antibody has (1) a heavy chain that has at least 95 percent sequence homology with SEQ ID NO: 11, and (2) a light chain that has at least 95 percent sequence homology with SEQ ID NO: 12. In some even more specific embodiments, each IgG antibody has (1) a heavy chain that has at least 98 percent sequence homology with SEQ ID NO: 11, and (2) a light chain that has at least 98 percent sequence homology with SEQ ID NO: 12. In some very specific embodiments, each IgG antibody has (1) a heavy chain that has at least 99 percent sequence homology with SEQ ID NO: 11, and (2) a light chain that has at least 99 percent sequence homology with SEQ ID NO: 12.

In some embodiments, each IgG antibody has (1) a heavy chain that has at least 90 percent sequence identity with SEQ ID NO: 11, and (2) a light chain that has at least 90 percent sequence identity with SEQ ID NO: 12. In some specific embodiments, each IgG antibody has (1) a heavy chain that has at least 95 percent sequence identity with SEQ ID NO: 11, and (2) a light chain that has at least 95 percent sequence identity with SEQ ID NO: 12. In some even more specific embodiments, each IgG antibody has (1) a heavy chain that has at least 98 percent sequence identity with SEQ ID NO: 11, and (2) a light chain that has at least 98 percent sequence identity with SEQ ID NO: 12. In some very specific embodiments, each IgG antibody has (1) a heavy chain that has at least 99 percent sequence identity with SEQ ID NO: 11, and (2) a light chain that has at least 99 percent sequence identity with SEQ ID NO: 12.

In some embodiments, each IgG antibody comprises two heavy chains and two light chains, wherein each of the two heavy chains has at least 90 percent sequence homology with SEQ ID NO: 11, and each of the two light chains has at least 90 percent sequence homology with SEQ ID NO: 12. In some specific embodiments, each IgG antibody comprises two heavy chains and two light chains, wherein each of the two heavy chains has at least 95 percent sequence homology with SEQ ID NO: 11, and each of the two light chains has at least 95 percent sequence homology with SEQ ID NO: 12. In some even more specific embodiments, each IgG antibody comprises two heavy chains and two light chains, wherein each of the two heavy chains has at least 98 percent sequence homology with SEQ ID NO: 11, and each of the two light chains has at least 98 percent sequence homology with SEQ ID NO: 12. In some very specific embodiments, each IgG antibody comprises two heavy chains and two light chains, wherein each of the two heavy chains has at least 99 percent sequence homology with SEQ ID NO: 11, and each of the two light chains has at least 99 percent sequence homology with SEQ ID NO: 12.

In some embodiments, each IgG antibody comprises two heavy chains and two light chains, wherein each of the two heavy chains has at least 90 percent sequence identity with SEQ ID NO: 11, and each of the two light chains has at least 90 percent sequence identity with SEQ ID NO: 12. In some specific embodiments, each IgG antibody comprises two heavy chains and two light chains, wherein each of the two heavy chains has at least 95 percent sequence identity with SEQ ID NO: 11, and each of the two light chains has at least 95 percent sequence identity with SEQ ID NO: 12. In some even more specific embodiments, each IgG antibody comprises two heavy chains and two light chains, wherein each of the two heavy chains has at least 98 percent sequence identity with SEQ ID NO: 11, and each of the two light chains has at least 98 percent sequence identity with SEQ ID NO: 12. In some very specific embodiments, each IgG antibody comprises two heavy chains and two light chains, wherein each of the two heavy chains has at least 99 percent sequence identity with SEQ ID NO: 11, and each of the two light chains has at least 99 percent sequence identity with SEQ ID NO: 12.

In some embodiments, each IgG antibody comprises at least four variable domains, wherein: the first and second variable domains are paired in the antibody such that the first and second variable domains bind a first cancer-associated antigen, and the antibody comprises a third variable domain and a fourth variable domain that are paired in the antibody such that the third and fourth variable domains bind a second cancer-associated antigen. Such antibodies include, for example, IgG-like bispecific antibodies. Examples of bispecific antibodies include amivantamab, glofitamab, talquetamab, and teclistamab. Those of ordinary skill in the art are capable of manufacturing homodimeric antibodies that comprise bispecific antibodies, for example, by cross-linking known bispecific antibodies.

In this disclosure, the term "paired" refers a spatial proximity and orientation between VH and VL regions that allow the VH and VL regions to simultaneously bind an epitope. VH and VL regions may be paired, for example, in a Fab by quaternary structure that includes one or more disulfide bonds and non-covalent interactions between the heavy chain constant domain CH1 and the light chain constant domain CL.

In some embodiments, each IgG antibody is a bispecific antibody that comprises CDRs that have sequence homology with the amino acid sequences set forth in SEQ ID NO: 3-6. A bispecific antibody may comprise amino acid sequences that have, for example, at least 90, 95, 97, 98, or 99 percent sequence homology with the sequences set forth in SEQ ID NO: 3-6 or at least 90, 95, 97, 98, or 99 percent sequence identity with the sequences set forth in SEQ ID NO: 3-6.

Various aspects of this disclosure relate to a pharmaceutical composition comprising an immunotherapeutic as described anywhere in this disclosure and a pharmaceutically acceptable carrier. Suitable pharmaceutically acceptable carriers generally include water with dissolved solutes that buffer pH and provide metal cations and an ionic strength that stabilize an immunotherapeutic of this disclosure. Such formulations are generally sterile, and the selection and preparation of such pharmaceutically acceptable carriers are well known. Solid formats including lyophilized therapeutics generally include, for example, metal cations, anions, and optionally polyols such as sugars (for example, trehalose or glucose) that stabilize the therapeutic in the solid phase and during its reconstitution into an aqueous format. General guidance on selecting pharmaceutically acceptable carriers is available, for example, in REMINGTON: THE SCIENCE AND PRACTICE OF PHARMACY, 22nd edition (Allen Jr, Loyd V., editor) Pharmaceutical Press, 2012, and the skilled practitioner will also look to the formulations of IgG antibodies described in this disclosure as well as other existing therapeutics in selecting a pharmaceutically acceptable carrier. Such guidance is generally available in the scientific literature and on existing product labels.

In some embodiments, the pharmaceutical composition is suitable for administration to a subject. In some specific embodiments, the pharmaceutical composition is suitable for administration to a human patient. In some very specific embodiments, the pharmaceutical composition is suitable for intravenous administration to a human patient.

Various aspects of this disclosure relate to a kit, comprising (1) a hermetically-sealed container that contains the pharmaceutical composition as described anywhere in this specification and (2) instructions for use of the pharmaceutical composition.

Various aspects of this disclosure relate to a medical device, comprising the pharmaceutical composition as described anywhere in this specification. In some embodiments, the medical device is a syringe, a venous cannula, or a drug-eluting implant.

Various aspects of this disclosure relate to a method of treating or preventing cancer in a subject, comprising identifying that the subject comprises cells that ectopically express the cancer-associated antigen and administering a pharmaceutical composition as described anywhere in this disclosure. Determining that the subject comprises cells that ectopically express the cancer-associated antigen include, for example, identifying mRNA that encodes the cancer-associated antigen by RT-PCR and identifying expression of the cancer-associated antigen by flow cytometry and/or immunohistochemistry. Such methods may advantageously allow determination that a cancer cell expresses the cancer-associated antigen, for example, based upon the prior selection of one or more cancer cells for analysis or based upon the co-identification of expression of the cancer-associated antigen and a cancer phenotype such as the co-expression of the cancer-associated antigen and another cancer antigen.

Various aspects of this disclosure relate to a method to modulate cells that express the cancer-associated antigen in a human subject, comprising administering the immunotherapeutic to the human subject, wherein the immunotherapeutic is a homodimeric antibody that comprises two IgG antibodies as described anywhere in this disclosure. In some embodiments, the method is a method of treating or preventing cancer in a human subject. In some specific embodiments, the method is a method of treating or preventing cancer in a human subject, the human subject presents with cancer, and at least a portion of the cells that express the cancer-associated antigen are cancer cells.

In some embodiments the immunotherapeutic is administered at an effective amount that is effective to induce cell death in at least a portion of the cells that express the cancer-associated antigen. In some specific embodiments, the immunotherapeutic comprises an Fc region, and the method induces cell death by Fc-receptor-mediated binding and activation of one or more leukocytes to the cells that express the cancer-associated antigen. In some specific embodiments, the immunotherapeutic is conjugated to a radioactive isotope, and the method induces cell death by emitting radiation within or in proximity to the cells that the cancer-associated antigen. In some specific embodiments, the immunotherapeutic is conjugated to a pharmaceutical agent, the pharmaceutical agent is cytotoxic, and the method induces cell death by releasing the pharmaceutical agent within or in proximity to the cells that express the cancer-associated antigen. In some very specific embodiments, the immunotherapeutic is conjugated to a pharmaceutical agent by a labile linker, the pharmaceutical agent is cytotoxic, and the method induces cell death by releasing the pharmaceutical agent within or in proximity to the cells that express the cancer-associated antigen.

In some embodiments, the subject is a mammal. In some specific embodiments, the subject is a rodent, lagomorph, feline, canine, porcine, ovine, caprine, *lama*, bovine, equine, or primate. In some very specific embodiments, the subject is a human patient.

In some embodiments, the subject is male or female. In some specific embodiments, the subject is female. In some specific embodiments, the subject is male.

In some embodiments, the subject presents with ectopic expression of the cancer-associated antigen. In some specific embodiments, the subject presents with cancer, and cells of the cancer express the cancer-associated antigen.

In some embodiments, the method comprises identifying that the subject comprises cells that express the cancer-associated antigen.

In some embodiments, the method comprises identifying that the subject comprises cells that express the cancer-associated antigen, wherein the cells that express the cancer-associated antigen comprise leukocytes, and the cancer is a lymphoma, leukemia, or myeloma. In some specific embodiments, the method comprises identifying that the subject comprises cells that express the cancer-associated antigen, wherein the cells that express the cancer-associated antigen comprise plasma cells, and the cancer is multiple myeloma. In some specific embodiments, the method comprises identifying that the subject comprises cells that express the cancer-associated antigen, wherein the cells that express the cancer-associated antigen comprise lymphocytes, and the cancer is lymphoma. In some specific embodiments, the method comprises identifying that the subject comprises cells that express the cancer-associated antigen, wherein the cells that express the cancer-associated antigen comprise ovarian cells, and the cancer is ovarian cancer. In some specific embodiments, the method comprises identifying that the subject comprises cells that express the cancer-associated antigen, wherein the cells that express the cancer-associated antigen comprise lung epithelial cells, and the cancer is non-small cell lung cancer.

In some embodiments, the method comprises identifying that a tissue sample of the human subject comprises either RNA encoding the cancer-associated antigen or a protein that includes the cancer-associated antigen prior to the administering.

In some embodiments, the tissue sample is a blood sample.

In some embodiments, the tissue sample is a biopsy. In some specific embodiments, the tissue sample is a tumor biopsy. In some very specific embodiments, the tissue sample is a bone marrow biopsy. In some very specific embodiments, the tissue sample is an ovarian biopsy. In some very specific embodiments, the tissue sample is a lung biopsy.

In some embodiments, the method comprises identifying that the tissue sample comprises a cancer biomarker, wherein the cancer biomarker is neither RNA encoding the cancer-associated antigen nor the cancer-associated antigen.

In some embodiments, the cells that express the cancer-associated antigen comprise leukocytes, and the cancer is a lymphoma, leukemia, or myeloma. In some specific embodiments, the cells that express the cancer-associated antigen comprise leukocytes, and the cancer is multiple myeloma or lymphoma. In some very specific embodiments, the cells that express the cancer-associated antigen comprise plasma cells, and the cancer is multiple myeloma. In some very specific embodiments, the cells that express the cancer-associated antigen comprise lymphocytes, and the cancer is lymphoma.

In some embodiments, the cells that express the cancer-associated antigen comprise ovarian cells, and the cancer is ovarian cancer.

In some embodiments, the cells that express the cancer-associated antigen comprise lung epithelial cells, and the cancer is non-small cell lung cancer.

In some embodiments, the administering is selected from intravenous, intramuscular, subcutaneous, intradermal, intraocular, parenteral, intraperitoneal, intrathecal, intralesional, and intratumoral administration. In some specific embodiments, the administering is intravenous administration.

Having described various features of this disclosure both generally and specifically in the preceding detailed description, the following exemplification provides specific examples of the preparation of the subject matter described herein. By way of these examples, and in the context of the preceding detailed description, the skilled person will immediately recognize variations to the methods set forth in the examples. The following exemplification is illustrative only and shall not limit this disclosure or any patent claim that matures from this disclosure. Any patent claim that matures from this disclosure shall instead be limited by the explicit features recited in the claim in the context of its claim dependency and according to conventional principles of claim construction as applied in view of this disclosure.

EXEMPLIFICATION

Example 1. Identification of Human Variable Regions for an Anti-Sp17 Antibody Based on Human Diversity A Fab phage display library was constructed from peripheral blood obtained from 120 healthy human donors. Briefly, this library was constructed by randomly combining nucleotide sequences encoding immunoglobulin heavy chain variable regions with nucleotide sequences encoding immunoglobulin light chain variable regions. The library had a diversity of approximately 1 trillion combinations. Bio-panning of the library identified twelve positive colonies, and nucleotide sequencing of the colonies identified two distinct clones. A single clone was identified as binding Sp17 by ELISA. The nucleotide sequences of the human VH and VL regions of the antibody are set forth in Table 1 below. The variable regions have the amino acid sequences set forth in Table 2 below and the CDRs set forth in Table 3 below.

TABLE 1

Nucleotide sequences of anti-Sp17 VH and VL regions identified by bio-panning a Fab phage-display library of ~1 trillion human Fabs developed from peripheral blood samples of 120 human subjects

| SEQ ID NO. | Region | Sequence |
|---|---|---|
| 1 | VH | CAGGTACAGCTGCAGCAGTCAGGGGCTGAGGTGAAGAAGCCTGGGTCCTC GGTGAAGGTCTCCTGCAAGGCTTCTGGAGGCACCTTCAGCAGCTATGCTA TCAGCTGGGTGCGACAGGCCCCTGGACAAGGGCTTGAGTGGATGGGAAGG ATCATCCCTATCCTTGGTATAGCAAACTACGCACAGAAGTTCCAGGGCAG AGTCACGATTACCGCGGACAAATCCACGAGCACAGCCTACATGGAGCTGA GCAGCCTGAGATCTGAGGACACGGCCGTGTATTACTGTGCGAGACCCTCC GAAGAGGTGGTAGCTGCTTACGGTGCTTTTGATATCTGGGGCCAAGGGAC CACGGTCACCGTCTCAAGC |
| 2 | VL | GAAATTGTGCTGACTCAGTCTCCACTCTCCCTGCCCGTCAGACCTGGGGA GCCGGCCTCCATCTCCTGCAGGGCTAGTCAGAGCCTCCTGCGTAGTGACG GATTCAACTACTTGGATTGGTACCTGCAGAAGCCAGGGCAGTCTCCACAG CTCCTGGTCTATTTGGGTTCTAATCGGGCCTCCGGGGTCCCTGACAGGTT CAGTGGCAGTGGATCAGGCACAGATTTTACACTGAAAATCAGCAGAGTGG AGGCTGAGGATGTTGGGGTTTATTACTGCATGCAAGCTGTACAAACTCCG TACATTTTTGGCCAGGGGACCAAGCTGGAGATCAAA |

TABLE 2

Amino acid sequences of anti-Sp17 VH and VL regions identified by bio-panning a Fab phage-display library of ~1 trillion human Fabs developed from peripheral blood samples of 120 human subjects

| SEQ ID NO. | Region | Sequence |
|---|---|---|
| 3 | VH | QVQLQQSGAEVKKPGSSVKVSCKASGGTFSSYAISWVRQAPGQGLEWMGR IIPILGIANYAQKFQGRVTITADKSTSTAYMELSSLRSEDTAVYYCARPS EEVVAAYGAFDIWGQGTTVTVSS |

TABLE 2-continued

Amino acid sequences of anti-Sp17 VH and VL regions
identified by bio-panning a Fab phage-display library
of ~1 trillion human Fabs developed from peripheral
blood samples of 120 human subjects

| SEQ ID NO. | Region | Sequence   10        20        30        40<br>1234567890123456789012345678901234567890 |
|---|---|---|
| 4 | VL | EIVLTQSPLSLPVRPGEPASISCRASQSLLRSDGFNYLDWYLQKPGQSPQ<br>LLVYLGSNRASGVPDRFSGSGSGTDFTLKISRVEAEDVGVYYCMQAVQTP<br>YIFGQGTKLEIK |

TABLE 3

Amino acid sequences of CDRs of the VH and VL
regions identified by bio-panning a Fab phage-
display library of ~1 trillion human Fabs
developed from peripheral blood samples of
120 human subjects

| SEQ ID NO. | Region | Sequence 10<br>12345678901234567 |
|---|---|---|
| 5 | VH CDR1 | GGTFSSYAIS |
| 6 | VH CDR2 | RIIPILGIANYAQKFQG |
| 7 | VH CDR3 | ARPSEEVVAAYGAFDI |
| 8 | VL CDR1 | RASQSLLRSDGFNYLD |
| 9 | VL CDR2 | LGSNRAS |
| 10 | VL CDR3 | MQAVQTPYIF |

Figure 2:
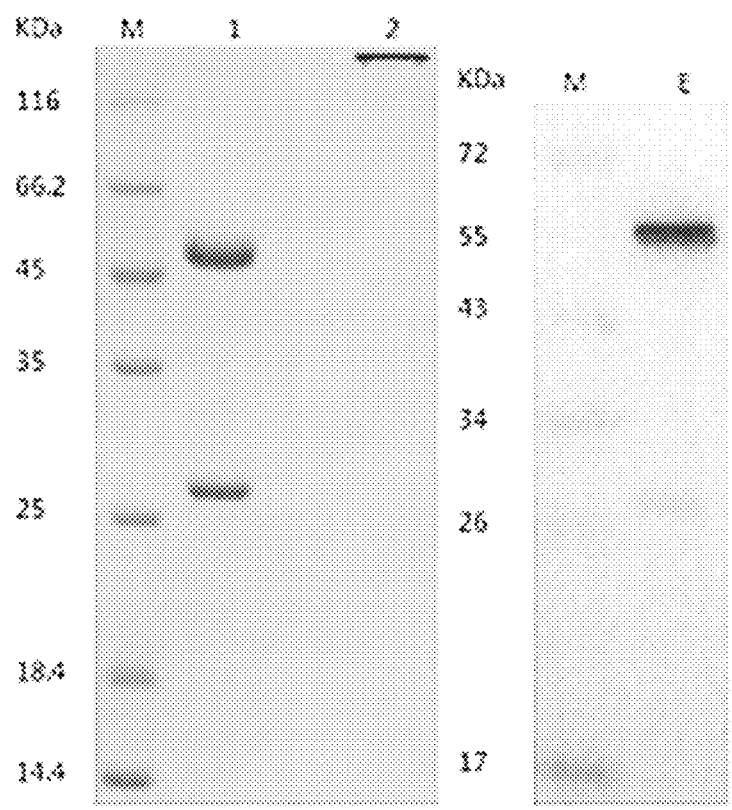
FIG. 2 consists of two panels. The left panel is a Coomassie-blue stained sodium dodecyl sulfate polyacrylamide gel electrophoresis (SDS-PAGE) gel loaded with a molecular weight standard (lane M), the anti-Sp17 antibody chAB2 under reducing conditions (lane 1), and the anti-Sp17 antibody chAB2 under non-reducing conditions (lane 2). The right panel is a western blot of an SDS-PAGE gel loaded with a molecular weight standard (lane M) and the anti-Sp17 antibody chAB2 under reducing conditions (lane E), in which chAB2 was detected using enhanced chemiluminescence (ECL) with anti-mouse secondary antibodies.
Figure 3:
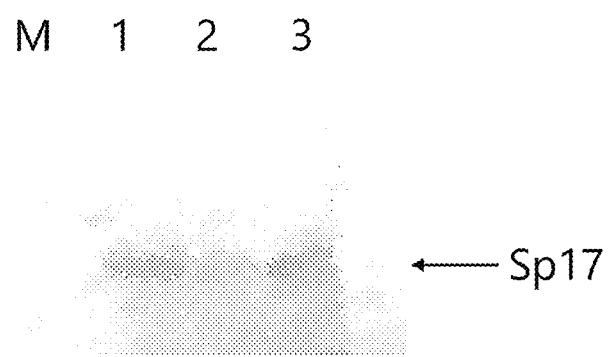
FIG. 3 is a western blot of an SDS-PAGE gel loaded with a molecular weight standard (lane M) and with Sp17 protein (lanes 1, 2, & 3), in which the Sp17 protein was detected with the anti-Sp17 antibody chAB2.
Figure 4:
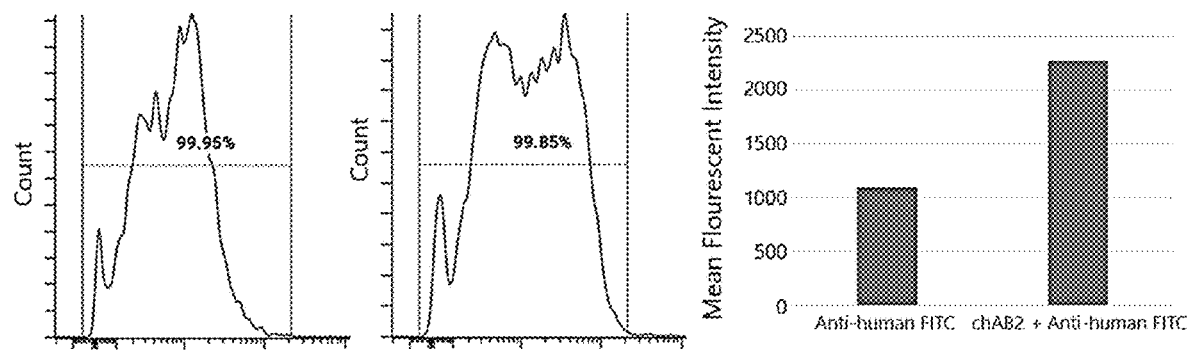
FIG. 4 consists of three panels. The left panel is a graph that depicts flow cytometry results for ID8 cells incubated with an anti-mouse fluorescein isothiocyanate (FITC) antibody, but without a primary antibody. The middle panel is a graph that depicts flow cytometry results for ID8 cells labeled with the anti-Sp17 antibody chAB2 and the anti-mouse FITC antibody. The right panel is a histogram that displays an increased mean fluorescence intensity for the ID8 cells labeled with chAB2 and the anti-mouse FITC antibody of the middle panel relative to ID8 cells incubated with the anti-mouse FITC antibody alone of the left panel.
Figure 5:
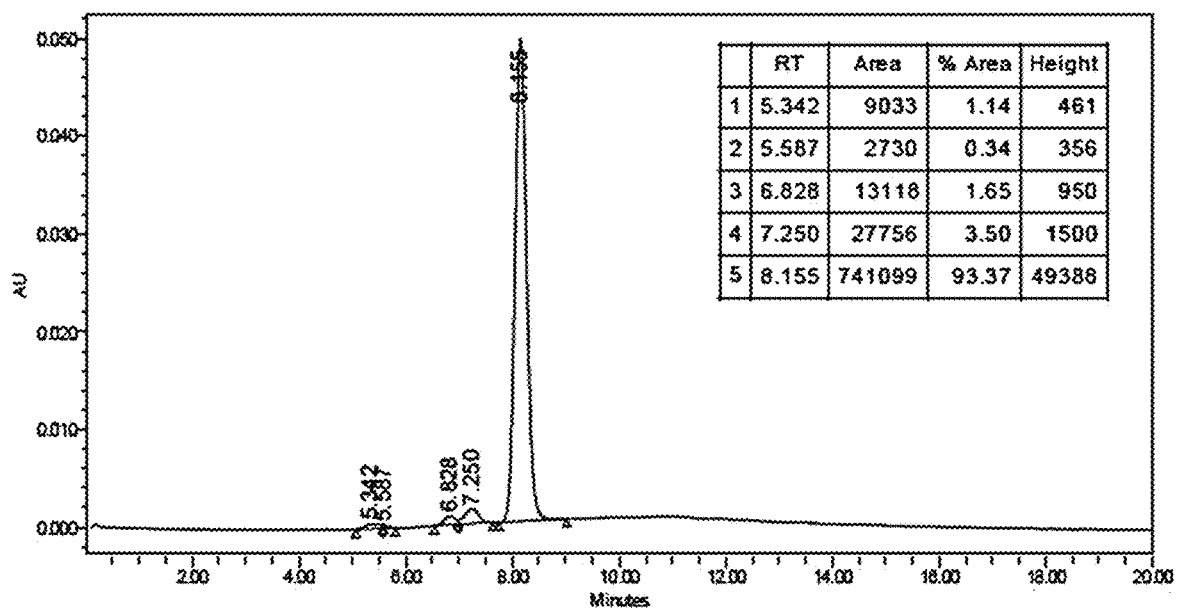
FIG. 5 is a high-performance liquid chromatography (HPLC) chromatogram that demonstrates that anti-Sp17 antibody chAB2 preparations can be manufactured at 93 percent purity.
Figures 6, 7:
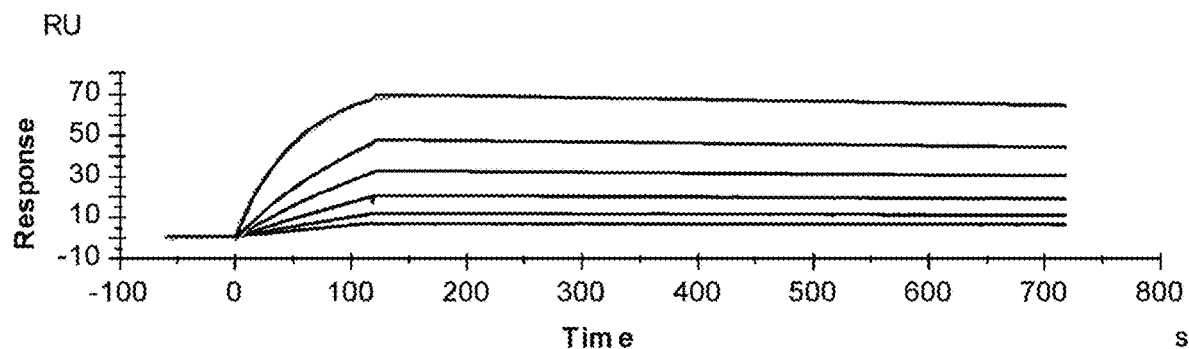
FIG. 6 is a graph that displays surface plasmon resonance data for the anti-Sp17 antibody chAB2 binding to a recombinant 6His-Sp17 protein. The lines correspond, from highest to lowest, to fitted cycles for 300 nanomolar, 100 nanomolar, 50 nanomolar, 25 nanomolar, 12.5 nanomolar, and 6.25 nanomolar concentrations of 6His-Sp17. This data was used to calculate an association rate constant (ka) for chAB2 to Sp17 of 62,600 per mole per second, a dissociation rate constant (kd) of 0.000 129 8 per second, and a dissociation constant (KD) of 2.073 nanomolar.
FIG. 7 is an image of an SDS-PAGE gel loaded with a molecular weight standard (lane M) and the anti-Sp17 antibody SP17-AB2 under reducing conditions (lane 1) and non-reducing conditions (lane 2).

Example 2. Engineering a Mouse-Human Chimeric Anti-Sp17 IgG2a/KAPPA Monoclonal Antibody The nucleotide sequences encoding the VH and VL regions of Example 1 were cloned into a mouse IgG2a heavy chain gene and a mouse kappa light chain gene, respectively, and expressed in CHO-S cells to produce a mouse-human chimeric antibody, which was named chAB2. Successful generation of the antibody was confirmed by SDS-PAGE and western blotting using anti-mouse heavy and light chain antibodies and recombinant Sp17 protein (FIGS. 2 & 3). The chAB2 antibody was reactive to mouse surface Sp17 protein expressed on the mouse ovarian cancer cell line ID8 (FIG. 4). HPLC of the chAB2 antibody preparation showed 93 precent purity (FIG. 5). Surface plasmon resonance with a Biacore™ T200 was used to determine a KD for chAB2 and Sp17 of 2.073 nanomolar (FIG. 6).

The specificity of the chAB2 antibody for Sp17 was determined with immunohistochemistry on a normal tissue microarray, which consisted of 33 normal tissues obtained from 2-3 human donors per tissue. The normal tissues included brain, eye, adrenal gland, hypophyseal, thyroid, parathyroid, tonsil, thymus, spleen, heart, lung, larynx, esophagus, stomach, small intestine, colon, liver, pancreas, salivary gland, kidney, bone, skeletal, skin, peripheral nerve, mesothelial, breast, ovary, endometrium, cervix, testis, and prostate. The chAB2 antibody bound to testis and did not bind to normal tissues.

Example 3. Engineering a Human Anti-Sp17 IgG4/KAPPA Monoclonal Antibody

Figure 8:
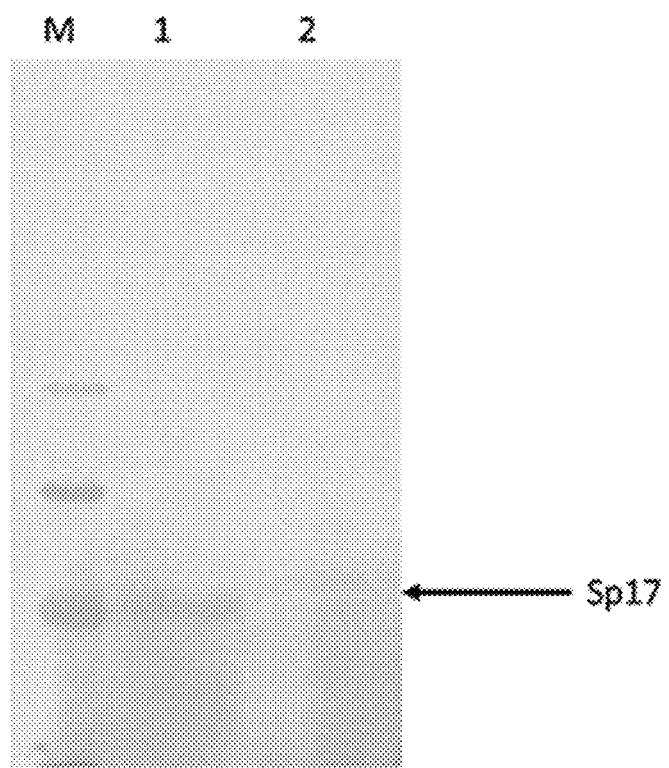
FIG. 8 is a western blot of an SDS-PAGE gel loaded with a molecular weight standard (lane M), with Sp17 protein (lane 1), and with a tumor cell lysate (lane 2), in which the Sp17 protein was detected with the anti-Sp17 antibody SP17-AB2.

The VH and VL nucleotide sequences of Example 1 were cloned into a human IgG4 heavy chain gene and a human kappa light chain gene, respectively. A S228P mutation was introduced in the heavy chain to reduce non-specific Fc receptor gamma binding. The resultant antibody was named SP17-AB2. Successful cloning was confirmed by sequence analysis. The amino acid sequences of the heavy chain and light chain are shown in Table 4, and the S228P mutation is underlined in SEQ ID NO: 11. Successful expression of the SP17-AB2 antibody was confirmed by SDS-PAGE (FIG. 7), and the ability of the SP17-AB2 antibody to bind Sp17 protein was confirmed by western blot (FIG. 8).

TABLE 4

Amino Acid Sequences of the human anti-Sp17 antibody SP17-AB2

| SEQ ID NO. | Region | Sequence   10        20        30        40<br>1234567890123456789012345678901234567890 |
|---|---|---|
| 11 | Full Heavy Chain | MDMRVPAQLLGLLLLWLRGARCQVQLQQSGAEVKKPGSSVKVSCKASGGT<br>FSSYAISWVRQAPGQGLEWMGRIIPILGIANYAQKFQGRVTITADKSTST<br>AYMELSSLRSEDTAVYYCARPSEEVVAAYGAFDIWGQGTTVTVSSASTKG<br>PSVFPLAPCSRSTSESTAALGCLVKDYFPEPVTVSWNSGALTSGVHTFPA<br>VLQSSGLYSLSSVVTVPSSSLGTKTYTCNVDHKPSNTKVDKRVESKYGPP<br>CPPCPAPEFLGGPSVFLFPPKPKDTLMISRTPEVTCVVVDVSQEDPEVQF<br>NWYVDGVEVHNAKTKPREEQFNSTYRVVSVLTVLHQDWLNGKEYKCKVSN<br>KGLPSSIEKTISKAKGQPREPQVYTLPPSQEEMTKNQVSLTCLVKGFYPS<br>DIAVEWESNGQPENNYKTTPPVLDSDGSFFLYSRLTVDKSRWQEGNVFSC<br>SVMHEALHNHYTQKSLSLSLGK |
| 12 | Full Light Chain | MDMRVPAQLLGLLLLWLRGARCEIVLTQSPLSLPVRPGEPASISCRASQS<br>LLRSDGFNYLDWYLQKPGQSPQLLVYLGSNRASGVPDRFSGSGSGTDFTL<br>KISRVEAEDVGVYYCMQAVQTPYIFGQGTKLEIKRTVAAPSVFIFPPSDE<br>QLKSGTASVVCLLNNFYPREAKVQWKVDNALQSGNSQESVTEQDSKDSTY<br>SLSSTLTLSKADYEKHKVYACEVTHQGLSSPVTKSFNRGEC |

TABLE 4-continued

Amino Acid Sequences of the human anti-Sp17 antibody SP17-AB2

```
SEQ
ID       Sequence   10        20        30        40
NO. Region         1234567890123456789012345678901234567890

13  Signal    MDMRVPAQLLGLLLLWLRGARC
    Peptide
```

Example 4. Methods to Prepare Homodimeric Antibodies that are Crosslinked with a Disulfide Bond The VH and VL nucleotide sequences of Example 1 were cloned into a human IgG1 heavy chain gene and a human kappa light chain gene, respectively.

Figure 9A:
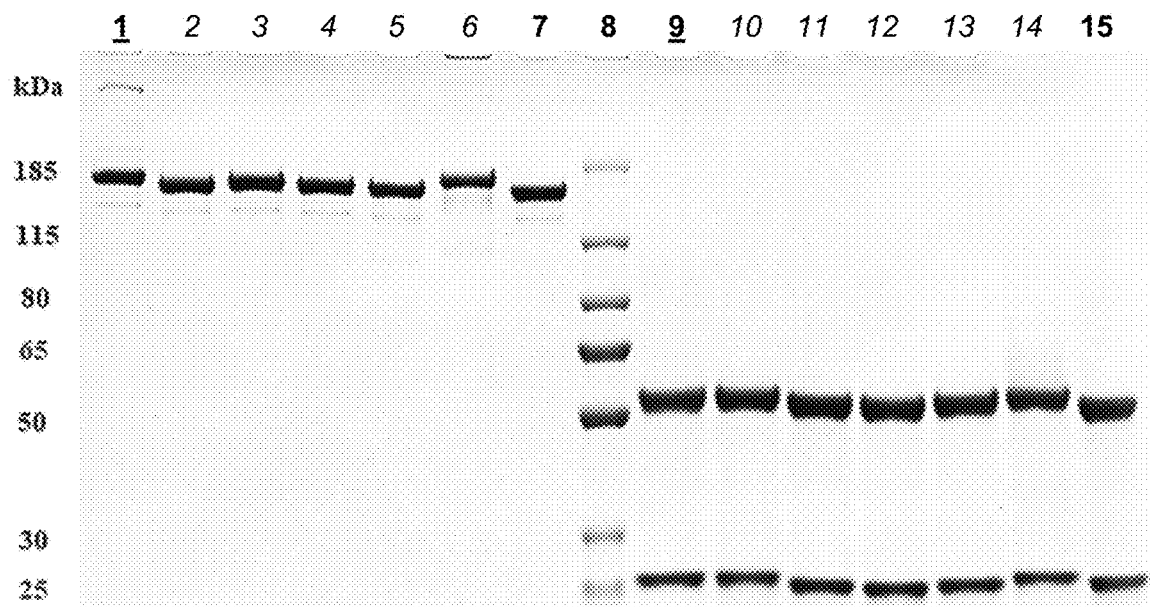
FIG. 9A is an image of a SDS-PAGE gel of a first IgG used to manufacture a chimeric antibody of this disclosure, in which lane 1 was loaded with 1 microgram of the first IgG under non-reducing conditions, lane 7 was loaded with 1 microgram of a control IgG under non-reducing conditions, lane 8 was loaded with a molecular weight standard, lane 9 was loaded with 2 micrograms of the first IgG under reducing conditions, and lane 15 was loaded with 2 micrograms of the control IgG under reducing conditions.
Figure 9B:
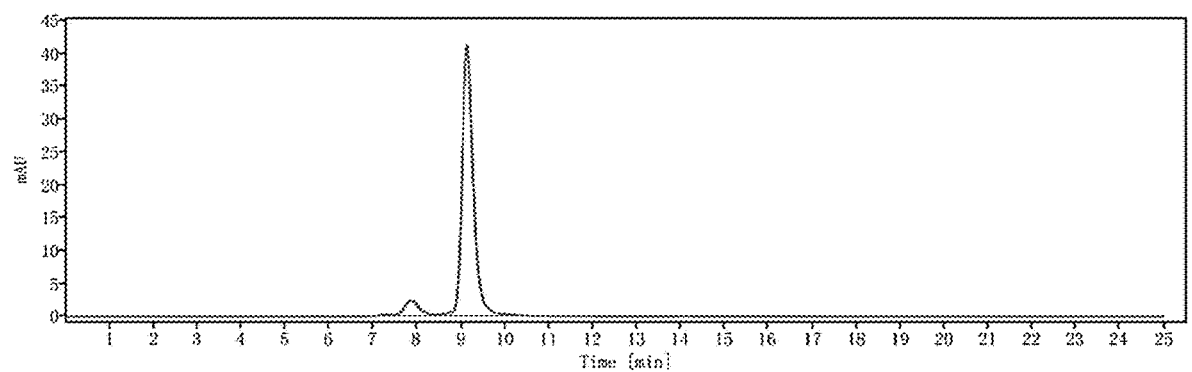
FIG. 9B is a chromatography trace monitored at 280 nanometers for liquid chromatography performed on the first IgG, which suggests that the first IgG had a purity of about 91.96 percent.

A first IgG1 comprising F405L and S444C mutations was cloned, expressed, and purified. The positions of F405L and S444C are defined according to EU numbering as set forth in Kabat. An SDS-PAGE analysis of the first IgG1 is shown in FIG. 9A, in which lane 1 corresponds to 1 microgram of the first IgG1 loaded under non-reducing conditions, lane 7 corresponds to 1 microgram of an IgG standard loaded under non-reducing conditions, lane 8 corresponds to a molecular weight standard, lane 9 corresponds to 2 micrograms of the first IgG1 loaded under reducing conditions, and lane 15 corresponds to 2 micrograms of an IgG standard loaded under reducing conditions. The first IgG1 displayed a purity of about 91.96 percent as determined by liquid chromatography and shown in FIG. 9B.

Figure 10A:
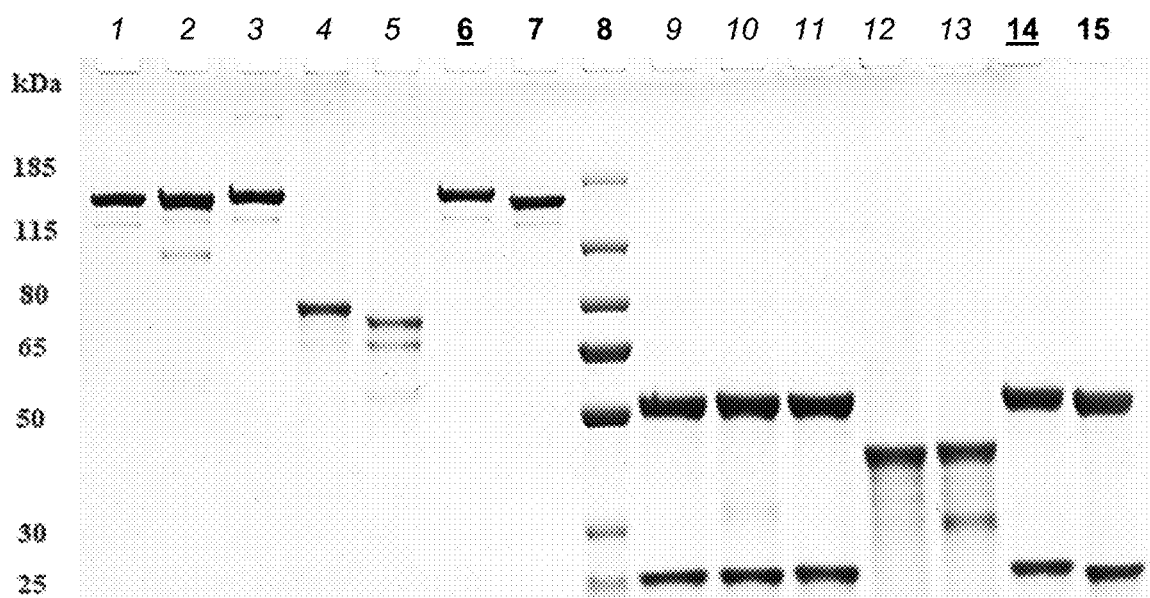
FIG. 10A is an image of an SDS-PAGE gel of a second IgG used to manufacture a chimeric antibody of this disclosure, in which lane 6 was loaded with 1 microgram of the second IgG under non-reducing conditions, lane 7 was loaded with 1 microgram of a control IgG under non-reducing conditions, lane 8 was loaded with a molecular weight standard, lane 14 was loaded with 2 micrograms of the second IgG under reducing conditions, and lane 15 was loaded with 2 micrograms of the control IgG under reducing conditions.
Figure 10B:
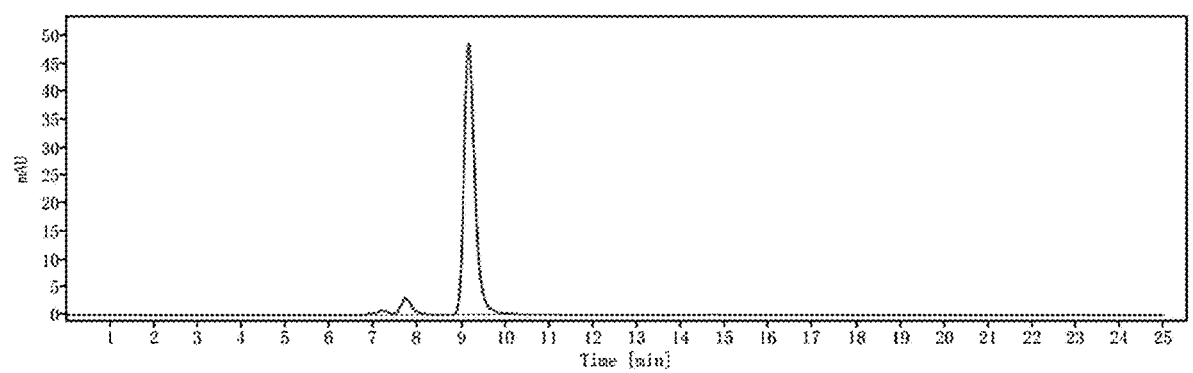
FIG. 10B is a chromatography trace monitored at 280 nanometers for liquid chromatography performed on the second IgG, which suggests that the second IgG had a purity of about 92.39 percent.

A second IgG1 comprising a K409R mutation was also cloned, expressed, and purified. The position of K409R is defined according to EU numbering as set forth in Kabat. An SDS-PAGE analysis of the second IgG1 is shown in FIG. 10A, in which lane 6 corresponds to 1 microgram of the second IgG1 loaded under non-reducing conditions, lane 7 corresponds to 1 microgram of an IgG standard loaded under non-reducing conditions, lane 8 corresponds to a molecular weight standard, lane 14 corresponds to 2 micrograms of the second IgG1 loaded under reducing conditions, and lane 15 corresponds to 2 micrograms of an IgG standard loaded under reducing conditions. The second IgG1 displayed a purity of about 92.39 percent as determined by liquid chromatography and shown in FIG. 10B.

The amino acid sequences of the first IgG1 and the second IgG1 were identical except for the F405L and S444C mutations of the first IgG1 and the K409R mutation of the second IgG1.

0.5 milligrams of the first IgG1 in 193.8 microliters and 0.5 milligrams of the second IgG1 in 204.9 microliters were combined, and then 44.3 microliters of 750 millimolar cysteamine was added to result in a reaction mixture with 443 microliters total volume containing 0.5 milligrams of the first IgG1 (about 7.5 millimolar), 0.5 milligrams of the second IgG1 (about 7.5 millimolar), and 75 millimolar cysteamine. The reaction mixture was incubated at 31 degrees Celsius for five hours to selectively reduce the disulfide bonds in the IgG1 hinge regions to allow for dissociation of the IgG1s into half molecules and recombination of the half molecules of the first IgG1 and the second IgG1 into chimeric IgG1s. The F405L and K409R mutations favored dissociation of the half molecules of the first IgG1 and the second IgG1, respectively, and permitted recombination of the half molecules into chimeric IgG1s to drive an equilibrium that favored formation of chimeric IgG1s from half molecules of the first IgG1 and the second IgG1 rather than recombination of the half molecules back into the original first IgG1 and second IgG1.

Following the five hours, the reaction mixture was transferred into dialysis bags with a 10 kilodalton molecular weight cut-off (10 kDa MWCO), and the dialysis bags were transferred into 5 liters of phosphate-buffered saline (PBS) adjusted to a pH of 7.4. The first round of dialysis proceeded for four hours. The dialysis bags were then transferred into a fresh 5 liters of PBS (pH 7.4) and dialyzed overnight at 4 degrees Celsius. The slightly alkaline pH of 7.4 allowed for an equilibrium in which some cysteines of the chimeric IgG1s were deprotonated to allow for spontaneous oxidation of (1) cysteines in the hinge region of the chimeric IgG1 to form disulfide bonds that crosslink half molecules of the first IgG1 and the second IgG1 in the chimeric IgG1 and (2) the S444C cysteines of different chimeric IgG1s to form homodimeric antibodies.

Following dialysis, the reaction mixture was transferred into microcentrifuge tubes, and 100 microliters of 100 millimolar cysteine was added to the reaction mixture to block remaining free cysteines. The blocked reaction mixture was then transferred back into dialysis bags with a 10 kDa MWCO, and the dialysis bags were transferred into 5 liters of 20 millimolar phosphate buffer (PB) adjusted to a pH of 6.0. The first round of dialysis proceeded for four hours, and then the dialysis bags were transferred into a fresh 5 liters of PB (pH 6.0) for a second four-hour round of dialysis.

Figure 11A:
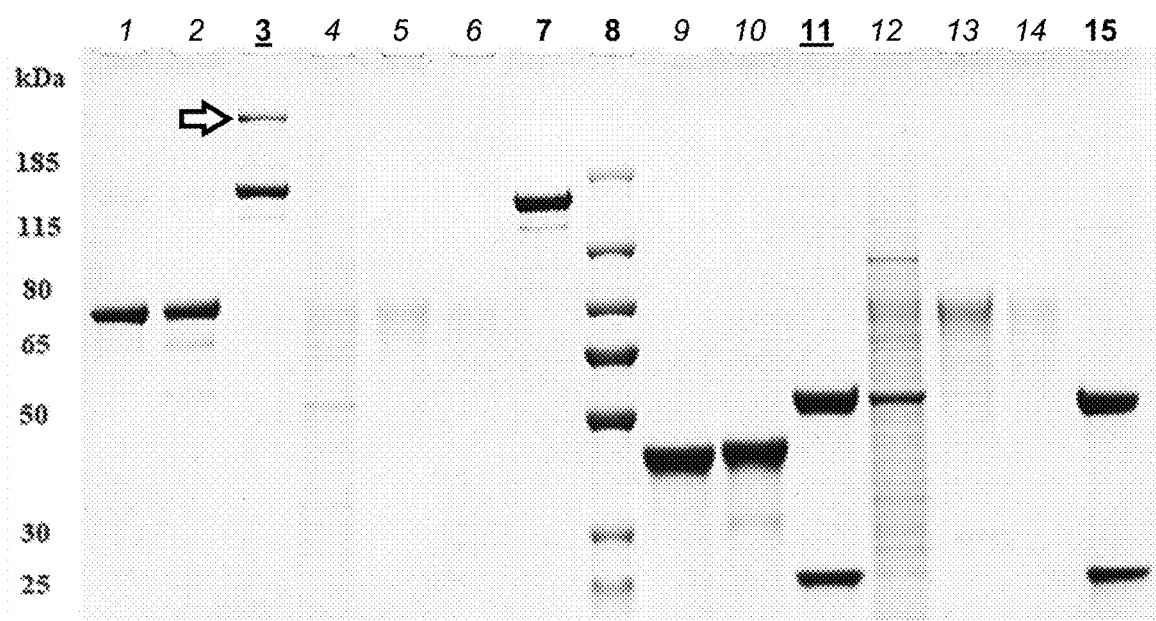
FIG. 11A is an image of an SDS-PAGE gel of monomers and homodimers of a chimeric IgG of this disclosure, in which lane 3 was loaded with 1 microgram of the chimeric IgG under non-reducing conditions, lane 7 was loaded with 1 microgram of a control IgG under non-reducing conditions, lane 8 was loaded with a molecular weight standard, lane 11 was loaded with 2 micrograms of the chimeric IgG under reducing conditions, and lane 15 was loaded with 2 micrograms of the control IgG under reducing conditions. The arrow denotes homodimers of the chimeric IgG visualized on the gel.

An SDS-PAGE analysis of the reaction mixture is shown in FIG. 11A, in which lane 3 corresponds to 1 microgram of protein from the reaction mixture loaded under non-reducing conditions, lane 7 corresponds to 1 microgram of an IgG standard loaded under non-reducing conditions, lane 8 corresponds to a molecular weight standard, lane 11 corresponds to 2 micrograms of protein from the reaction mixture loaded under reducing conditions, and lane 15 corresponds to 2 micrograms of an IgG standard loaded under reducing conditions. The arrow in FIG. 11A depicts a protein band that displays a molecular weight that corresponds to the molecular weight of the homodimeric antibody. Liquid chromatography was used to determine that about 28.16 percent of the protein in the reaction mixture displayed a molecular weight consistent with the homodimeric antibody.

Figure 11B:
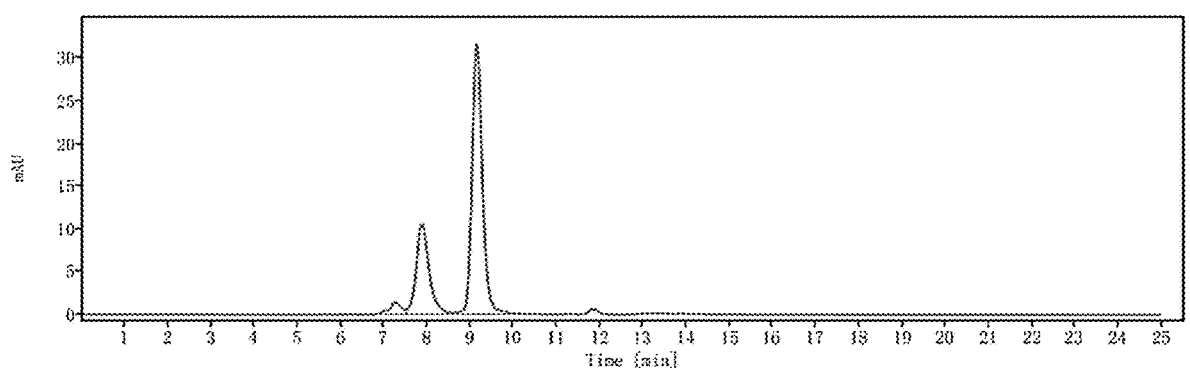
FIG. 11B is a chromatography trace monitored at 280 nanometers for liquid chromatography performed on a reaction mixture used to prepare a homodimeric antibody of this disclosure. The chromatography trace suggests that protein of the reaction mixture contains about 28.16 percent by mass of the homodimeric antibody.
Figure 12A:
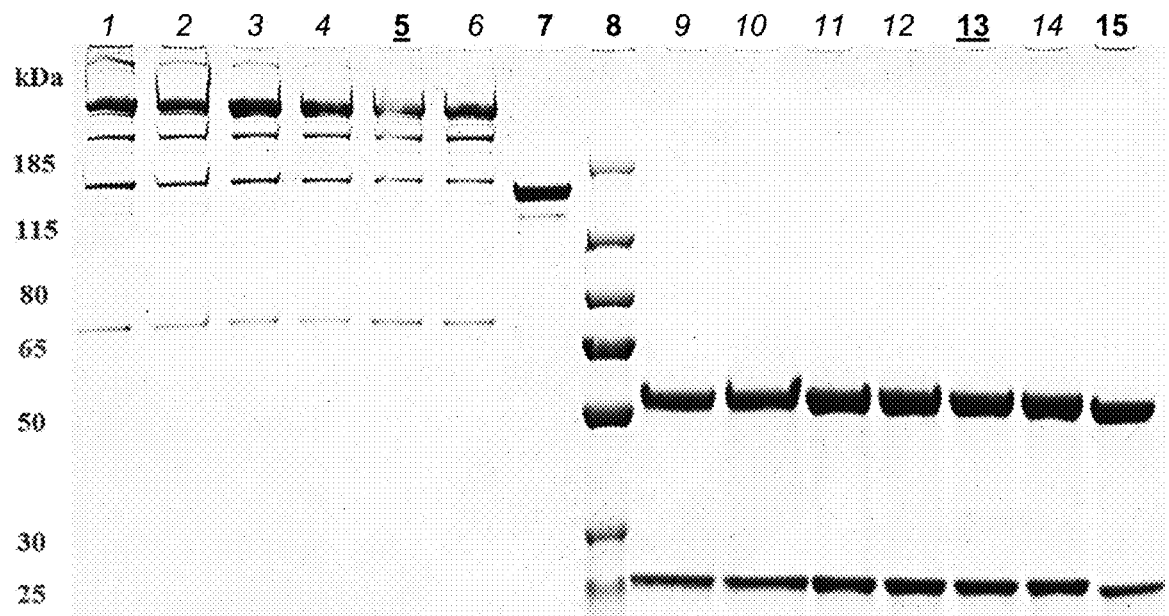
FIG. 12A is an image of an SDS-PAGE gel of homodimeric antibodies of this disclosure, in which lanes 1 through 6 each correspond to 1 microgram total protein from homodimeric antibodies purified by size-exclusion chromatography under non-reducing conditions, lane 7 corresponds to 1 microgram of an IgG standard loaded under non-reducing conditions, lane 8 corresponds to a molecular weight standard, lanes 9 through 14 each correspond to 2 micrograms total protein from homodimeric antibodies purified by size-exclusion chromatography under reducing conditions, and lane 15 corresponds to 2 micrograms of an IgG standard loaded under reducing conditions.
Figure 12B:
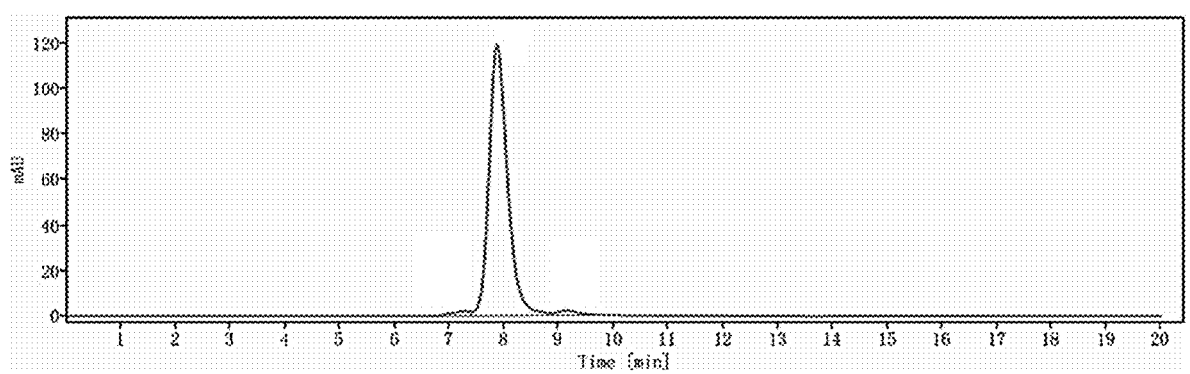
FIG. 12B is a chromatography trace monitored at 280 nanometers for liquid chromatography performed on a homodimeric antibody of this disclosure. The chromatography trace suggests that homodimeric antibody was about 96.17 percent pure.

The homodimeric antibody was then purified from monomeric antibodies using size-exclusion chromatography. An SDS-PAGE analysis of different fractions of the eluent from size-exclusion chromatography is depicted in FIG. 12A, in which lanes 1 through 6 each correspond to 1 microgram total protein from different, consecutive fractions of the eluent under non-reducing conditions, lane 7 corresponds to 1 microgram of an IgG standard loaded under non-reducing conditions, lane 8 corresponds to a molecular weight standard, lanes 9 through 14 each correspond to 2 micrograms total protein from different, consecutive fractions of the eluent under reducing conditions, and lane 15 corresponds to 2 micrograms of an IgG standard loaded under reducing conditions. Lanes 1 and 9 correspond to the same fraction, which was about 64.98 percent pure as determined by liquid chromatography. Lanes 2 and 10 correspond to the same fraction, which was about 84.54 percent pure as determined by liquid chromatography. Lanes 3 and 11 correspond to the same fraction, which was about 92.62 percent pure as determined by liquid chromatography. Lanes 4 and 12 correspond to the same fraction, which was about 94.86 percent pure as determined by liquid chromatography. Lanes 5 and 13 correspond to the same fraction, which was about 96.17 percent pure as determined by liquid chromatography. Lanes 6 and 14 correspond to the same fraction, which was about 96.61 percent pure as determined by liquid chromatography. A liquid chromatography trace corresponding to the homodimeric antibody of lanes 5 and 13 is shown in FIG. 12B, and its peak is centered at 7.9 minutes, which is the same retention time as the homodimeric antibody observed in FIG. 11B.

Example 5. Methods to Prepare Immunoconjugates of Homodimeric Antibodies

Eluents of Example 4 having a purity of at least 94 percent are transferred into phosphate-buffered saline (PBS; 0.1 molar phosphate and 0.15 molar sodium chloride at a pH of 7.4) at a concentration of 10 milligrams homodimeric antibody per milliliter. 20 milligrams of sulfo-SMCC (Thermo Scientific, Massachusetts, United States) is dissolved in 4 milliliters of distilled, deionized water to result in a sulfo-SMCC solution, which is immediately added to 20 milliliters of the homodimeric antibody solution to produce a sulfo-SMCC reaction. The sulfo-SMCC reaction is stirred for 2 hours at 4 degrees Celsius under argon to produce an activated homodimeric antibody. Excess sulfo-SMCC is then removed from the activated homodimeric antibody on a Sephadex G25 column equilibrated with 50 millimolar potassium phosphate/50 millimolar sodium chloride/2 millimolar ethylenediaminetetraacetate, pH 6.5. The activated homodimeric antibody is then diluted with 50 millimolar potassium phosphate/50 millimolar sodium chloride/2 millimolar ethylenediaminetetraacetate, pH 6.5, to a concentration of 10 milligrams activated homodimeric antibody per milliliter, which is combined with about 10 equivalents of DM1 (mertansine) from a 10 millimolar solution of DM1 dissolved in dimethylacetamide to produce a conjugation mixture. The conjugation mixture is stirred at ambient temperature under argon for 4 to about 16 hours to produce a dimeric immunoconjugate comprising a MCC linker and a DM1 pharmaceutical agent. Alternative methods to produce such immunoconjugates are described, for example, in United States Patent Application Publication No. 2023/0201210 A1, which is incorporated by reference in its entirety. A control, monomeric immunoconjugate comprising a MMC linker and a DM1 pharmaceutical agent is produced using an analogous strategy.

Example 6. Immunoconjugates of the Homodimeric Antibody Display Enhanced Cytotoxicity Against Ovarian Cancer Cells An immunoconjugate of the homodimeric antibody of Example 4 was prepared using a method similar to that described in Example 5. The drug-to-antibody ratio of the immunoconjugate was determined to be about 5.52 units of DM1 per homodimeric antibody. A control immunoconjugate of the monomeric IgG1 of Example 4 was also prepared using a method similar to that described in Example 5. The control, monomeric immunoconjugate was determined to have a drug-to-antibody ratio of about 2.95 units of DM1 per monomeric antibody.

Figure 13:
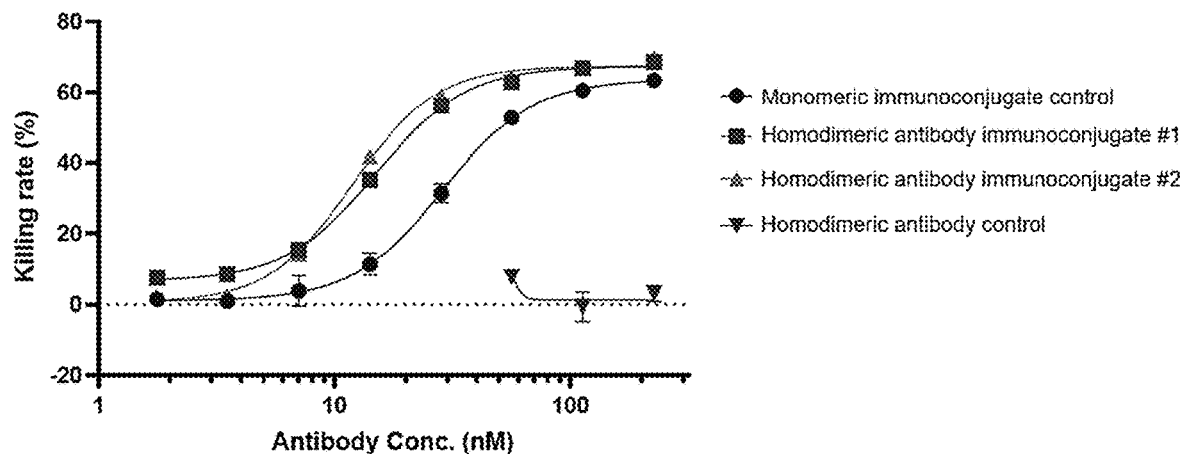
FIG. 13 is a graph that depicts cytotoxicity against SKOV3 cells of an immunotherapeutic of this disclosure (■, ▲), which comprises a homodimeric antibody conjugated with pharmaceutical agent DM1, relative to a control homodimeric antibody (▼) that was not conjugated to a pharmaceutical agent and relative to a monomeric antibody control (●) that was also conjugated to DM1.
Figure 14:
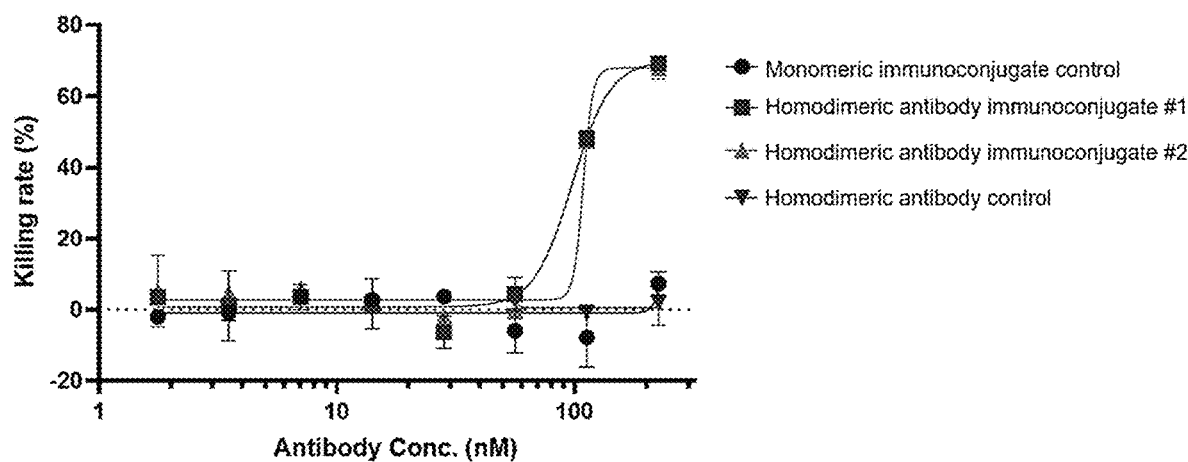
FIG. 14 is a graph that depicts cytotoxicity against Luci-ID8 cells of an immunotherapeutic of this disclosure (■, ▲), which comprises a homodimeric antibody conjugated with pharmaceutical agent DM1, relative to a control homodimeric antibody (▼) that was not conjugated to a pharmaceutical agent and relative to a monomeric antibody control (●) that was also conjugated to DM1.

The immunoconjugate of the homodimeric antibody was added to SKOV3 cells at varying concentrations, and cytotoxicity was measured. SKOV3 cells are immortalized human ovarian cancer cells that express Sp17. The experiment was repeated with a second batch of the immunoconjugate of the homodimeric antibody, the naked homodimeric antibody, and the immunoconjugate of the monomeric IgG1. A graph that displays differences in cytotoxicity is shown in FIG. 13. The immunoconjugates of the homodimeric antibody displayed improved cytotoxicity relative to both the naked homodimeric antibody and the immunoconjugate of the monomeric IgG1.

The immunoconjugate of the homodimeric antibody was added to Luci-ID8 cells at varying concentrations, and cytotoxicity was measured. Luci-ID8 cells are immortalized murine ovarian cancer cells that express Sp17. The experiment was repeated with a second batch of the immunoconjugate of the homodimeric antibody, the naked homodimeric antibody, and the immunoconjugate of the monomeric IgG1. A graph that displays differences in cytotoxicity is shown in FIG. 13. The immunoconjugates of the homodimeric antibody displayed improved cytotoxicity relative to the naked homodimeric antibody and the immunoconjugate of the monomeric IgG1.

Example 7. Homodimeric Antibodies Crosslink Cells In Vitro

The monomeric IgG1 and the homodimeric antibody described in Example 4 are used to label ID8 cells, and crosslinking of the cells is assessed by flow cytometry. Forward scatter and side scatter indicates that the cells labeled with the homodimeric antibody include large populations that are consistent with crosslinked cells. The cells labelled with the monomeric IgG1 lack such large populations of cells. This data suggests that homodimeric antibodies may be used to crosslink cells.

Example 8. Homodimeric Antibodies Display Greater Cellular Uptake Relative to Monomeric Antibodies The monomeric IgG1 and the homodimeric antibody described in Example 4 are labeled with fluorescein isothiocyanate (FITC). ID8 cells at various cell densities are incubated with the FITC-labeled antibodies, washed, and then visualized by fluorescence microscopy. The cells incubated with monomeric IgG1 display FITC-associated fluorescence that is localized primarily to the cell peripheries regardless of confluency. Cells at or near 100 percent confluence that are incubated with the homodimeric antibody display FITC-associated fluorescence localized between different cells. Cells at less than 50 percent confluence that are incubated with the homodimeric antibody display significant FITC-associated fluorescence within the cytosol. These results suggest that homodimeric antibodies display increased cellular uptake relative to monomeric antibodies.

No patent claim that matures from this disclosure shall be interpreted as requiring any feature of the foregoing Exemplification. Any methods described in the claims or specification shall not be interpreted to require the steps to be performed in a specific order unless expressly stated otherwise. The methods shall be interpreted to provide support to perform the recited steps in any order unless expressly stated otherwise.

Certain features described in the context of separate implementations can also be implemented in combination in a single implementation. Conversely, various features that are described in the context of a single implementation can also be implemented in multiple implementations separately or in any suitable sub-combination. Moreover, although features may be described above in certain combinations and even initially claimed as such, one or more features from a claimed combination can be excised from the combination, and the claimed combination may be directed to a sub-combination or variation of a sub-combination.

The example configurations described in this document do not represent all the examples that may be implemented or that fall within the scope of the claims. The term "example" shall be interpreted to mean "serving as an example, instance, or illustration," and not "preferred" or "advantageous over other examples."

Articles such as "the," "a," and "an" can connote the singular or plural. The word "or" when used without a preceding "either" (or other similar language indicating that "or" is unequivocally meant to be exclusive, for example, only one of x or y) shall be interpreted to be inclusive (for example, "x or y" means one or both of x and y).

The term "and/or" shall also be interpreted to be inclusive (for example, "x and/or y" means one or both of x and y). In situations where "and/or" or "or" are used as a conjunction for a group of three or more items, then the group shall be interpreted to include one item alone, all the items together, or any combination or number of the items.

The terms "has," "contain(s)," and "include(s)" shall be interpreted to be synonymous with the term "comprise(s)" and as inclusive or open-ended such as to not exclude additional unrecited subject matter. Use of the four preceding terms also discloses and provides support for narrower alternative implementations, in which these terms are replaced by "consisting" or "consisting essentially of," which are closed as to exclude additional unrecited subject matter.

Unless otherwise indicated, all numbers or expressions, such as those expressing concentrations, ratios, counts, and the like, used in the specification (other than the claims) are understood to be modified in all instances by the term "approximately." At the very least, and not as an attempt to limit the application of the doctrine of equivalents to the claims, each numerical parameter recited in the specification or claims that is modified by the term "approximately" should be construed in light of the number of recited significant digits and by applying ordinary rounding techniques. All disclosed ranges are to be understood to encompass and provide support for claims that recite any subranges or any and all individual values subsumed by each range. For example, a stated range of "at least 90 percent" shall be construed as including support for at least 90 percent, at least 95 percent, at least 97 percent, at least 98 percent, at least 99 percent, at least 99.5 percent, at least 99.6 percent, at least 99.7 percent, at least 99.8 percent, and at least 99.9 percent.

The terms recited in the claims should be given their ordinary and customary meaning as determined by reference to relevant entries in widely used general dictionaries, relevant technical references, commonly understood meanings by those in the art, and the like with the understanding that the broadest meaning imparted by any one or combination of these sources should be given to the claim terms (for example, two or more relevant references should be combined to provide the broadest meaning of the combination of references) subject only to the following two exceptions: (a) when a term is used in a manner that is more expansive than its ordinary and customary meaning, then the term should be given its ordinary and customary meaning plus the additional expansive meaning, and (b) when a term has been explicitly defined to have a different meaning by reciting the term and its definition along with the phrase "in this disclosure" or similar language, then the term shall be limited to the definition (for example, this disclosure uses the word "chimeric" in reference to antibodies differently than as commonly used in the relevant arts, and the word "chimeric antibody" and similar words such as "chimeric IgG" shall be limited to the scope defined in this disclosure). References to specific examples shall not invoke the foregoing exception (b) or otherwise restrict the scope of the recited claim terms. Other than situations where the foregoing exception (b) applies, nothing contained in this document should be considered a disclaimer or disavowal of claim scope.

The subject matter recited in the claims is not coextensive with and should not be interpreted to be coextensive with any implementation, feature, or combination of features described or illustrated in this document. This is true even if only a single implementation of the feature or combination of features is illustrated and described.

The entire content of each document listed below is incorporated by reference into this document (the documents below are collectively referred to as the "incorporated documents"). If the same term is used in both this document and one or more of the incorporated documents, then the term should be interpreted to have the broadest meaning imparted by any one or combination of these sources unless the term has been explicitly defined to have a different meaning in this document. If there is an inconsistency between any incorporated document and this document, then this document shall govern. The incorporated subject matter should not be used to limit or narrow the scope of the explicitly recited or depicted subject matter.

U.S. Pat. No. 5,731,168 A, entitled "Method for making heteromultimeric polypeptides," granted Mar. 24, 1998;

U.S. Pat. No. 5,877,296 A, entitled "Process for preparing conjugates of methyltrithio antitumor agents," granted Mar. 2, 1999;

U.S. Pat. No. 6,565,827 B1, entitled "Radioimmunotherapy of lymphoma using anti-CD20 antibodies," granted May 20, 2003;

U.S. Pat. No. 7,422,739 A, entitled "Anti-CD20 antibodies," granted Sep. 9, 2008;

U.S. Pat. No. 8,088,387 B2, entitled "Method of targeting specific cell populations using cell-binding agent maytansinoid conjugates linked via a non-cleavable linker, said conjugates, and methods of making said conjugates," granted Jan. 1, 2012;

U.S. Pat. No. 8,592,562 B2, entitled "Method for making antibody Fc-heterodimeric molecules using electrostatic steering effects," granted Nov. 26, 2013;

U.S. Pat. No. 9,505,848 B2, entitled "Engineered heterodimeric protein domains," granted Nov. 29, 2016;

U.S. Pat. No. 9,862,769 B2, entitled "Monoclonal antibodies against HER2," granted Jan. 9, 2018;

U.S. Pat. No. 10,011,858 B2, entitled "Methods for producing polypeptides by regulating polypeptide association," granted Jul. 3, 2018;

U.S. Pat. No. 10,344,050 B2, entitled "Production of heterodimeric proteins," granted Jul. 9, 2019;

U.S. Pat. No. 10,597,464 B2, entitled "Heterodimeric antibody Fc-containing proteins and methods for production thereof," granted Mar. 24, 2020;

U.S. Patent Application Publication No. 2023/0201210 A1, entitled "Combinations of anti-her2 antibody-drug conjugate and chemotherapeutic agents, and methods of use," published Jun. 29, 2023;

Kabat, E. A. et al., "Sequences of proteins of immunological interest." 5th Edition—US Department of Health and Human Services, NIH publication No. 91-3242 (1991);

Shopes, B., "A genetically engineered human IgG mutant with enhanced cytolytic activity," THE JOURNAL OF IMMUNOLOGY, 1992 May 1; 148(9):2918-22;

Shopes, B., "A genetically engineered human IgG with limited flexibility fully initiates cytolysis via complement," MOLECULAR IMMUNOLOGY, 1993 April; 30(6):603-9; and van der Neut Kolfschoten, M. et al., "Anti-inflammatory activity of human IgG4 antibodies by dynamic Fab arm exchange," SCIENCE, 2007 Sep. 14; 317(5844):1554-7.

What is claimed is:

1. A method to treat cancer in a human subject, comprising administering a therapeutically effective amount of an immunotherapeutic to the subject, wherein:
   the immunotherapeutic comprises a homodimeric antibody and either a radioisotope or a labile pharmaceutical agent;
   the homodimeric antibody comprises two immunoglobulin G (IgG) antibodies that are covalently crosslinked;
   each IgG antibody comprises two antigen-binding sites that each specifically bind a cancer-associated antigen such that the homodimeric antibody comprises exactly four antigen-binding sites that each specifically bind the cancer-associated antigen, and
   each antigen-binding site binds Sp17 and comprises:
   a first variable domain that comprises a VH CDR1 region comprising the amino acid sequence set forth in SEQ ID NO: 5, a VH CDR2 region comprising the amino acid sequence set forth in SEQ ID NO: 6, and a VH CDR3 region comprising the amino acid sequence set forth in SEQ ID NO: 7; and
   a second variable domain that comprises a VL CDR1 region comprising the amino acid sequence set forth in SEQ ID NO: 8, a VL CDR2 region comprising the amino acid sequence set forth in SEQ ID NO: 9, and a VL CDR3 region comprising the amino acid sequence set forth in SEQ ID NO: 10.

2. The method of claim 1, wherein the immunotherapeutic is an immunoconjugate, and the homodimeric antibody is conjugated to the radioisotope.

3. The method of claim 2, wherein the radioisotope is selected from isactinium-225, astatine-211, bismuth-212, bismuth-213, copper-67, gallium-68, holmium-166, indium-111, iodine-124, iodine-131, lutetium-177, samarium-153, technetium-99, terbium-149, or yttrium-90.

4. The method of claim 1, wherein the immunotherapeutic is an immunoconjugate, and the homodimeric antibody is conjugated to a pharmaceutical agent by a labile linker forming the labile pharmaceutical agent.

5. The method of claim 4, wherein the pharmaceutical agent is selected from calicheamicin, camptothecin, deruxtecan, doxorubicin, emtansine, exatecan, irinotecan, maleimidocaproyl monomethyl auristatin F, mertansine, monomethyl auristatin F, paclitaxel, PE38, pyrrolobenzodiazepine, SN-38, and vedotin.

6. The method of claim 1, wherein:
a monomeric antibody that consists of the IgG antibody has a reference efficacy against the cancer;
the immunotherapeutic has an improved efficacy against the cancer;
the reference efficacy and the improved efficacy are determined by an in vitro cytotoxicity assay on cells that express the cancer-associated antigen; and
the improved efficacy is more than 100 percent more effective per mole than the reference efficacy.

7. The method of claim 1, wherein:
a monomeric antibody that consists of the IgG antibody has a reference infusion time, which is an amount of time necessary to infuse an effective amount of the monomeric antibody to treat the cancer;
the immunotherapeutic has a shorter infusion time, which is an amount of time necessary to infuse the effective amount of the immunotherapeutic to treat the cancer; and
the shorter infusion time is at least one hour shorter than the reference infusion time.

8. The method of claim 1, wherein each IgG antibody comprises a heavy chain variable region comprising the amino acid sequence set forth in SEQ ID NO: 3 and a light chain variable region comprising the amino acid sequence set forth in SEQ ID NO: 4.

9. The method of claim 8, wherein each IgG antibody comprises a heavy chain comprising the amino acid sequence set forth in SEQ ID NO: 11 and a light chain comprising the amino acid sequence set forth in SEQ ID NO: 12.

10. The method of claim 1, wherein the immunotherapeutic comprises a dissociation constant (KD) with human Sp17 of no greater than 25 nanomolar.

11. The method of claim 1, wherein each IgG antibody comprises a heavy chain constant region and a light chain constant region.

12. The method of claim 1, wherein the two IgG antibodies are covalently crosslinked in the homodimeric antibody with an engineered disulfide bond.

13. A method to treat cancer in a human subject, comprising administering to the subject a therapeutically effective amount of an immunotherapeutic, wherein:
the cancer comprises cells that express human sperm protein 17 (Sp17);
the immunotherapeutic comprises a homodimeric antibody that comprises two immunoglobulin G (IgG) antibodies that are covalently crosslinked;
each IgG antibody comprises two antigen-binding sites that each specifically bind Sp17 such that the homodimeric antibody comprises exactly four antigen-binding sites that each specifically bind Sp17; and
each IgG antibody comprises a heavy chain variable region comprising the amino acid sequence set forth in SEQ ID NO: 3 and a light chain variable region comprising the amino acid sequence set forth in SEQ ID NO: 4.

14. The method of claim 13, wherein each IgG antibody comprises a heavy chain comprising the amino acid sequence set forth in SEQ ID NO: 11 and a light chain comprising the amino acid sequence set forth in SEQ ID NO: 12.

15. An immunotherapeutic comprising a homodimeric antibody and either a radioisotope or a labile pharmaceutical agent, wherein:
the homodimeric antibody comprises two immunoglobulin G (IgG) antibodies that are covalently crosslinked;
each IgG antibody comprises two antigen-binding sites that each specifically bind a cancer-associated antigen such that the homodimeric immunoconjugate comprises exactly four antigen-binding sites that each specifically bind the cancer-associated antigen, and
each antigen-binding site binds Sp17 and comprises:
a first variable domain that comprises a VH CDR1 region comprising the amino acid sequence set forth in SEQ ID NO: 5, a VH CDR2 region comprising the amino acid sequence set forth in SEQ ID NO: 6, and a VH CDR3 region comprising the amino acid sequence set forth in SEQ ID NO: 7; and
a second variable domain that comprises a VL CDR1 region comprising the amino acid sequence set forth in SEQ ID NO: 8, a VL CDR2 region comprising the amino acid sequence set forth in SEQ ID NO: 9, and a VL CDR3 region comprising the amino acid sequence set forth in SEQ ID NO: 10.

16. The immunotherapeutic of claim 15, wherein the immunotherapeutic is an immunoconjugate, and the homodimeric antibody is conjugated to the radioisotope.

17. The immunotherapeutic of claim 16, wherein the radioisotope is actinium-225, astatine-211, bismuth-212, bismuth-213, copper-67, gallium-68, holmium-166, indium-111, iodine-124, iodine-131, lutetium-177, samarium-153, technetium-99, terbium-149, or yttrium-90.

18. The immunotherapeutic of claim 15, wherein the immunotherapeutic is an immunoconjugate, and the homodimeric antibody is conjugated to a pharmaceutical agent by a labile linker forming the labile pharmaceutical agent.

19. The immunotherapeutic of claim 18, wherein the pharmaceutical agent is selected from calicheamicin, camptothecin, deruxtecan, doxorubicin, emtansine, exatecan, irinotecan, maleimidocaproyl monomethyl auristatin F, mertansine, monomethyl auristatin F, paclitaxel, PE38, pyrrolobenzodiazepine, SN-38, and vedotin.

20. The immunotherapeutic of claim 15, wherein each IgG antibody comprises a heavy chain variable region comprising the amino acid sequence set forth in SEQ ID NO: 3 and a light chain variable region comprising the amino acid sequence set forth in SEQ ID NO: 4.

21. The immunotherapeutic of claim 15, wherein each IgG antibody comprises a heavy chain comprising the amino acid sequence set forth in SEQ ID NO: 11 and a light chain comprising the amino acid sequence set forth in SEQ ID NO: 12.

* * * * *